US009683967B2

(12) United States Patent
Lal et al.

(10) Patent No.: US 9,683,967 B2
(45) Date of Patent: Jun. 20, 2017

(54) INTEGRATED CIRCUITS BASED BIOSENSORS

(71) Applicant: Cornell University, Ithaca, NY (US)

(72) Inventors: Amit Lal, Ithaca, NY (US); Ved Gund, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/114,814

(22) PCT Filed: Jan. 27, 2015

(86) PCT No.: PCT/US2015/013154
§ 371 (c)(1),
(2) Date: Jul. 27, 2016

(87) PCT Pub. No.: WO2015/113072
PCT Pub. Date: Jul. 30, 2015

(65) Prior Publication Data
US 2016/0341697 A1    Nov. 24, 2016

Related U.S. Application Data

(60) Provisional application No. 61/932,234, filed on Jan. 27, 2014.

(51) Int. Cl.
*G01N 27/00* (2006.01)
*G01N 27/64* (2006.01)
*G01N 27/62* (2006.01)

(52) U.S. Cl.
CPC ........... *G01N 27/64* (2013.01); *G01N 27/622* (2013.01)

(58) Field of Classification Search
CPC .............................. G01N 27/64; G01N 27/622
(Continued)

(56) References Cited

U.S. PATENT DOCUMENTS

2005/0263790 A1    12/2005  Moon et al.
2008/0022755 A1*    1/2008  Shinbo ................. G01N 5/02
                                              73/31.06
(Continued)

OTHER PUBLICATIONS

Lee, H.G., Authorized Officer, Korean Intellectual Property Office, International Application No. PCT/US2015/013154, International Search Report and Written Opinion, May 14, 2015, 17 pages.

*Primary Examiner* — Michael Maskell
(74) *Attorney, Agent, or Firm* — Perkins Coie LLP

(57) ABSTRACT

Methods, systems, and devices are disclosed for implementing molecular sensors. In one aspect, an ion-gas sensor device includes a pre-concentration module to collect and concentrate a gas-phase chemical for analysis; a piezoelectric fan to produce an air-flow through acoustic streaming to drive the gas-phase chemical released by the pre-concentration module to one or more downstream modules; an ionizer downstream from the piezoelectric fan to ionize the gas-phase chemical; and a gas sensor downstream from the piezoelectric fan and the ionizer to detect the ionized gas-phase chemical driven by the piezoelectric fan. The piezoelectric fan can include a stack of thin-film layers that includes a thin-film piezoelectric layer. The ion-gas sensor device is made into an ultra-portable package capable of integration with mobile communication devices, such as PDA devices or smart phones.

35 Claims, 37 Drawing Sheets

(58) Field of Classification Search
USPC ......... 250/281, 282, 288; 977/701, 725, 837
See application file for complete search history.

(56) References Cited

U.S. PATENT DOCUMENTS

| | | |
|---|---|---|
| 2008/0216558 A1 | 9/2008 | Koyilothu et al. |
| 2010/0288014 A1 | 11/2010 | Yao et al. |
| 2013/0066349 A1 | 3/2013 | Fink et al. |
| 2014/0355381 A1* | 12/2014 | Lal ........................ B81B 3/0021 367/87 |

\* cited by examiner

Photo of IV measurement setup taken with Celestron USB microscope

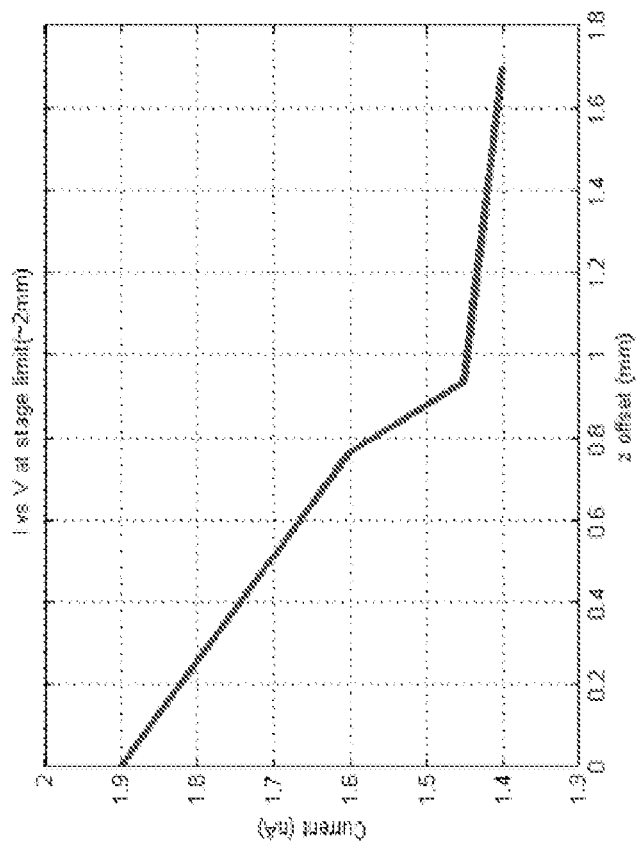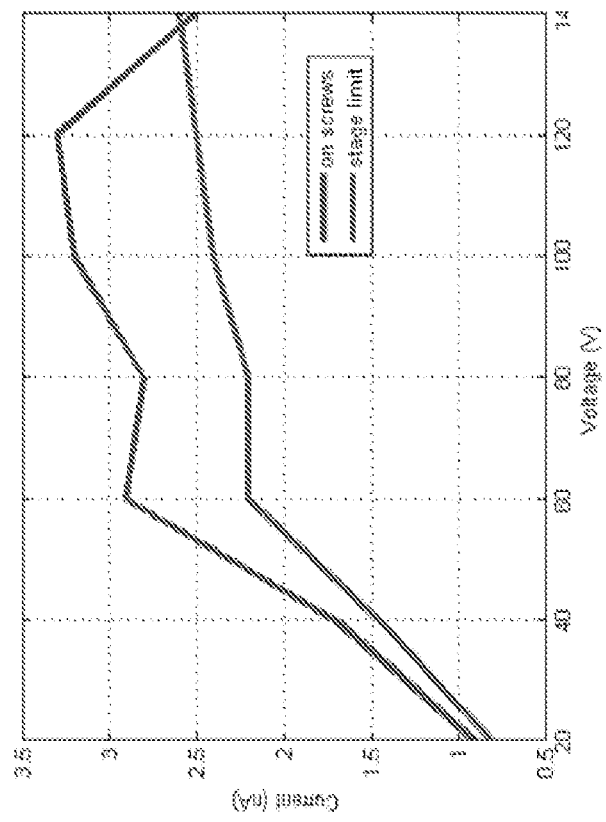
FIG. 16

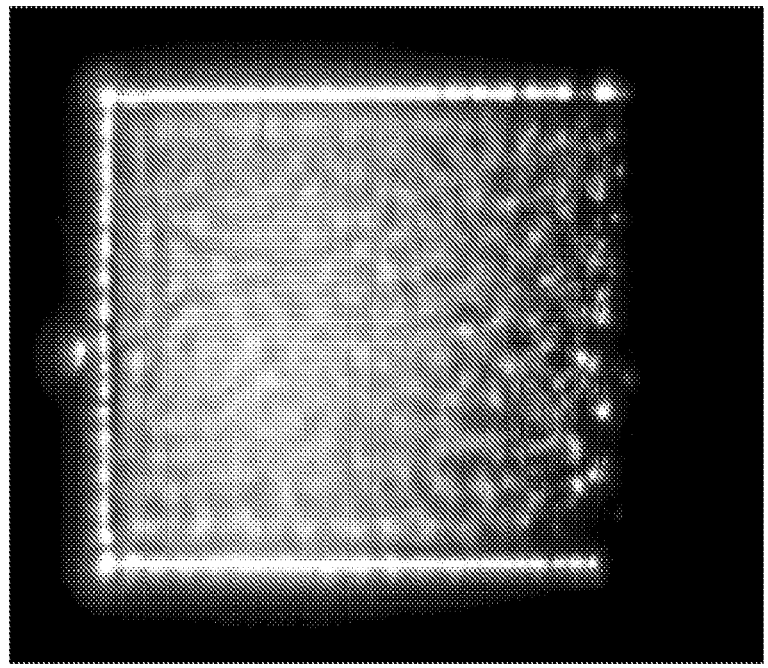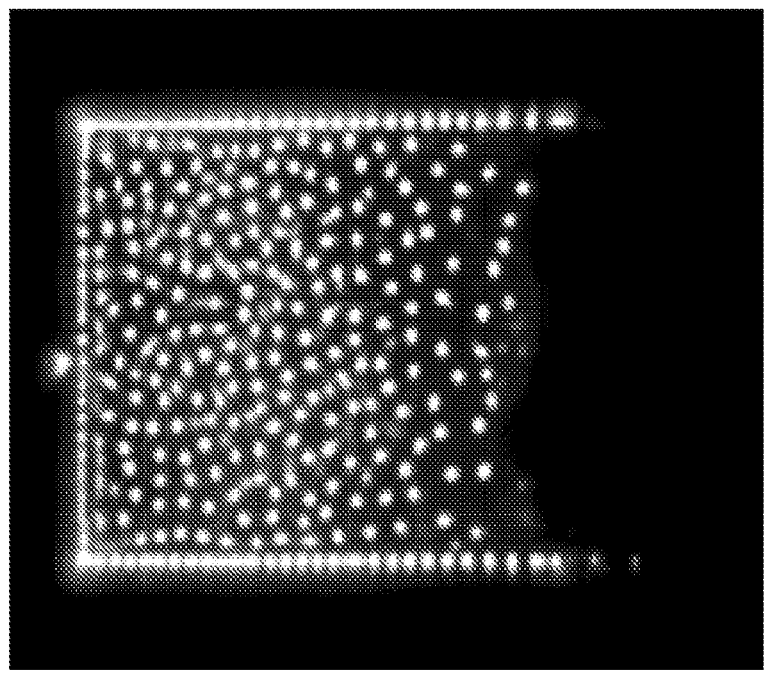
FIG. 21

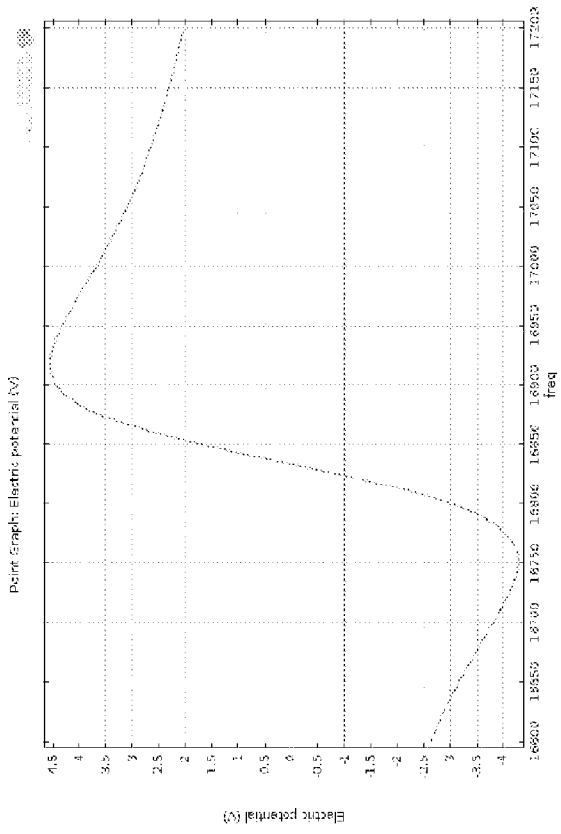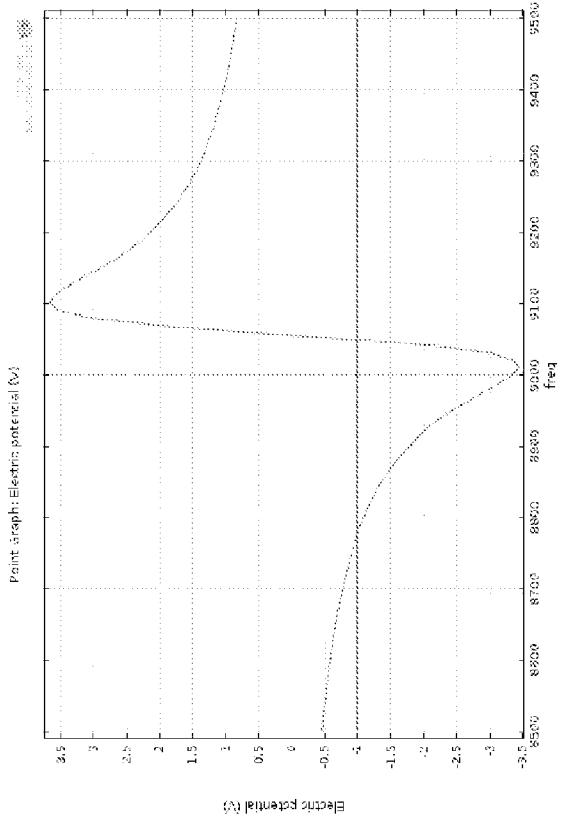
FIG. 24

Concentrate driving energy into output electrode

Output voltage (vs frequency)

| | | | | | |
|---|---|---|---|---|---|
| Micro pre-concentration | 200 | 2W | 0W (standby) | | 170mA (active) | - |
| Air pump | RT | 2 VAC | 48 µW | <20 µW | 24 µA (AC) | (based on other components) |
| Ionizer 1 – Ni63 | RT | 0 | 0 | 0 | 0 | 0 |
| Ionizer 2 – Pyroelectric LiNbO3 | 60 | 5 VDC | 800 µW | <500µW | 160 µA | (based on other components) |
| Ionizer 3 – PZT Transformer | RT | 5 VAC | 180 µW | <50µW | 36 µA (AC) | (based on other components) |
| MDS-IMS 1 – HALF-IMS | RT | 9 VDC, <10 µA 45 VDC, <10 µA | < 10 µW | | <1 µA | (based on other components) |
| MDS-IMS 2 & 3 – Vertical DMS & Tailored DMS | RT | 9 VDC, <10 µA 45 VDC, <10 µA | - | | - | (based on other components) |

FIG. 34

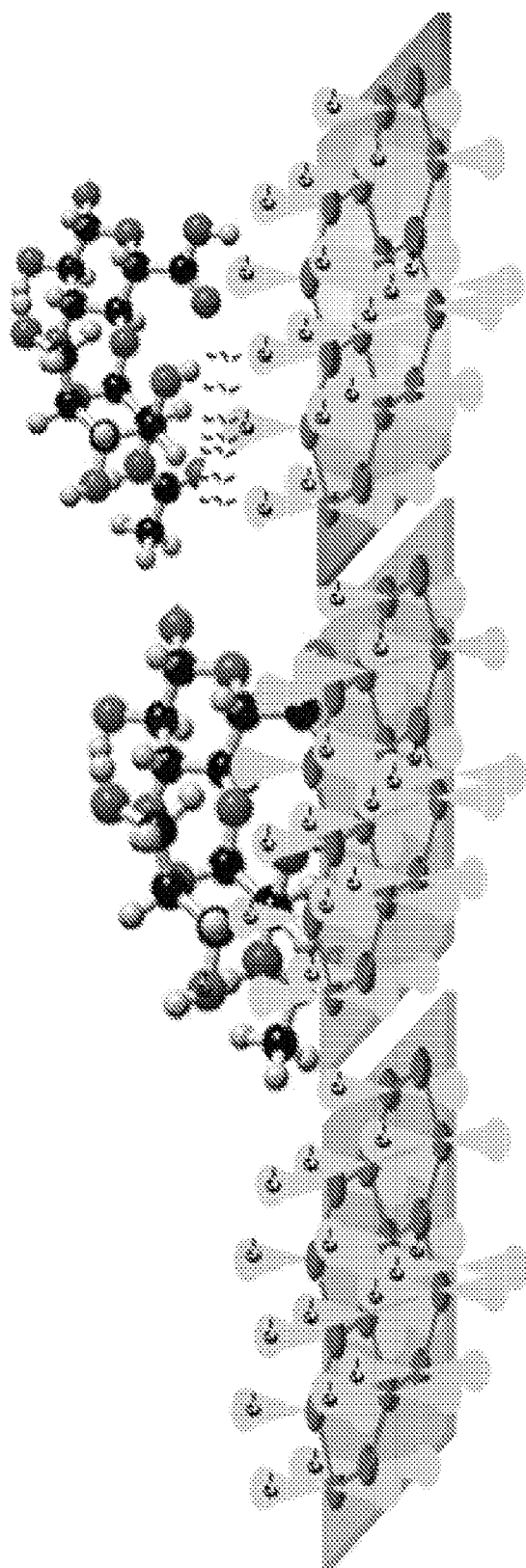

… (1) …

INTEGRATED CIRCUITS BASED BIOSENSORS

PRIORITY CLAIM AND RELATED PATENT APPLICATIONS

This patent document claims priority and the benefits of U.S. Provisional Application No. 61/932,234 entitled "INTEGRATED CIRCUITS BASED BIOSENSORS" and filed Jan. 27, 2014, the disclosure of which is incorporated by reference as part of the specification of this document.

TECHNICAL FIELD

This patent document relates to systems, devices, and processes that use molecular sensor technologies including a chip scale gas sensor capable of integration with mobile communication devices, such as PDA or smart phone devices.

BACKGROUND

A biological sensor or biosensor is an analytical tool that can detect a chemical, substance or organism using a biologically sensitive component coupled with a transducing element to convert a detection event into a signal for processing and/or display. Biosensors can use biological materials as the biologically sensitive component, e.g., such as biomolecules including enzymes, antibodies, aptamers, peptides, nucleic acids, etc., or small molecules such as carbohydrates, as well as virus and living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by a suitable transduction mechanism, for example, electrical, magnetic, mechanical, physicochemical, electrochemical, optical, piezoelectric, or others.

SUMMARY

Molecular sensor devices, systems, and techniques are disclosed for measuring ion-mobility to detect gases in ultra-portable packages capable of integration with mobile communication devices, such as PDA or smart phone devices. The power supply for the disclosed gas sensors can be the standard cell-phone battery. The disclosed sensors can include a piezoelectric micro fan that is low power, low voltage, and sufficiently small to provide air molecule samples at rates determined by convection. In other aspects, the disclosed sensor devices include a chip-size ionizer for gas analyte ionization.

In one aspect, an ion-gas sensor device is disclosed. This sensor device includes a substrate including an array of pillars and troughs; a microfan component including a first stack and a second stack of layers of a piezoelectric composite material formed on the pillars of the substrate and protruding over the troughs, the first stack of layers to sense the flow of ions in a gas and the second stack of layers actuate to drive the ions to a detection region of the device at a controlled flow rate; a layer of a radioactive material formed in the trough of the substrate to ionize the gas when flowed above the layer; and an array of electrode formed in the detection region to detect ion mobility of the ions of the gas. The ion-gas sensor device is made into an ultra-portable package capable of integration with mobile communication devices, such as PDA devices or smart phones.

In another aspect, another ion-gas sensor device is disclosed. This ion-gas sensor device includes: a pre-concentration module to collect and concentrate a gas-phase chemical for analysis; a piezoelectric fan to produce an air-flow through acoustic streaming to drive the gas-phase chemical released by the pre-concentration module to one or more downstream modules; an ionizer downstream from the piezoelectric fan to ionize the gas-phase chemical; and a gas sensor downstream from the piezoelectric fan and the ionizer to detect the ionized gas-phase chemical driven by the piezoelectric fan. The piezoelectric fan can include a stack of thin-film layers that includes a thin-film piezoelectric layer. The ion-gas sensor device is made into an ultra-portable package capable of integration with mobile communication devices, such as PDA devices or smart phones.

In yet another aspect, another ion-gas sensor device is disclosed. This ion-gas sensor device includes an integrated pre-concentration and ionization module that further includes a first material layer to collect and concentrate a gas-phase molecules for analysis and a second material layer underneath the first material layer to ionize the gas-phase molecules. The ion-gas sensor device also includes a piezoelectric fan to produce an air-flow through acoustic streaming to drive ionized gas-phase molecules released by the integrated pre-concentration and ionization module to one or more downstream modules. The ion-gas sensor device additionally includes a gas sensor downstream from the piezoelectric fan to detect the ionized gas-phase molecules driven by the piezoelectric fan. In some embodiments, the first material layer is a functionalized material for molecule collection and concentration and the second material layer is a $LiNbO_3$ crystal. The integrated pre-concentration and ionization module further includes a resistive heater placed underneath the second material layer. The heat generated by the resistive heater both triggers ionization of the gas-phase molecules adsorbed in the functionalized material by the ionization module and the ionized gas-phase molecules adsorbed in the functionalized material to be released from the functionalized material.

In yet another aspect, another ion-gas sensor device is disclosed. This ion-gas sensor device includes a pre-concentration module to collect and concentrate a gas-phase chemical for analysis; an integrated air pump and ionization module that includes a piezoelectric fan to produce an air-flow through acoustic streaming to drive the gas-phase chemical released by the pre-concentration module to one or more downstream modules. The piezoelectric fan includes a region configured to ionize the gas-phase chemical driven by the piezoelectric fan. This ion-gas sensor device also includes a gas sensor downstream from the integrated air pump and ionization module to detect the ionized gas-phase chemical driven by the piezoelectric fan. In some embodiments, the integrated air pump and ionization module includes a PZT high voltage transformer.

BRIEF DESCRIPTION OF THE DRAWINGS

FIG. 16 shows exemplary results of IV measurements (left plot) and IZ measurements (right plot) of an exemplary Ni-63 ionizer using the test setup shown in FIG. 14.

FIG. 21 shows light patterns of dielectric barrier discharge (DBD) at the surface of a piezo-transformer (PT) 1 minute after the onset of discharge (left image) and after continuous stable discharge (right image).

FIG. 24 shows COMSOL simulation results for sense-voltage produced (single-ended) with 1V AC signal applied to the drive electrodes for 450 um (left plot) and 900 um (right plot) wide PT beams. An isotropic loss factor of ~0.01 is assumed for these simulations.

FIG. 34 presents a table including power consumptions for different modules within the chip-based gas sensor.

FIG. 35A shows graphene patterned on micromachined suspended membranes.

FIG. 35B shows using graphene patterned micromachined suspended membranes as an electrical sensor to sense the mass of the adsorbed molecules without heating the structure.

FIG. 35C shows using graphene patterned micromachined suspended membranes as an mechanical sensor to sense the mass of the adsorbed molecules while heating the structure with a resistive heater.

Figure 1:
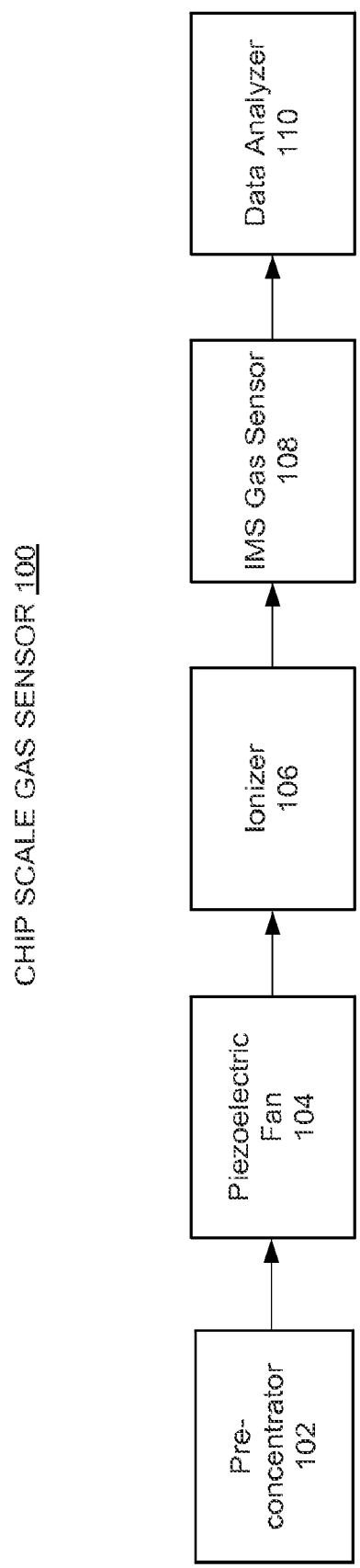
FIG. 1 shows a block diagram of an exemplary chip scale gas sensor of the disclosed technology.

Table 1 shows comparing piezoelectric fan designs with conventional fan designs.

Table 2 shows fan performance analysis (comparing thin film PZT fan with bulk PZT fan).

DETAILED DESCRIPTION

Molecular sensor devices, systems, and techniques are disclosed for measuring ion-mobility to detect gases in ultra-portable packages capable of integration with mobile communication devices, such as PDA devices or smart phones. The power supply for the disclosed gas sensors can be the standard cell-phone battery. The disclosed sensors can include a piezoelectric micro fan that is low power, low voltage, and sufficiently small to provide air molecule samples at rates determined by convection. In other aspects, the disclosed sensor devices include a chip-size ionizer for gas analyte ionization.

In some implementations, the disclosed molecular sensor devices include a chip-scale gas sensor using a low-voltage thin-film piezoelectric sense-actuate fan pair.

In some implementations, an ion-gas sensor device includes a substrate including an array of pillars and troughs, a micro-fan component including a first stack and a second stack of layers of a piezoelectric composite material formed on the pillars of the substrate and protruding over the troughs, the first stack of layers to sense the flow of ions in a gas and the second stack of layers actuate to drive the ions to a detection region of the device at a controlled flow rate, a layer of a radioactive material formed in the trough of the substrate to ionize the gas when flowed above the layer, and an array of electrode formed in the detection region to detect ion mobility of the ions of the gas. The ion-gas sensor device is made into an ultra-portable package capable of integration with mobile communication devices, such as PDA devices or smart phones.

In another aspect, an ion-gas sensor device is disclosed. This ion-gas sensor device includes: a pre-concentration module to collect and concentrate a gas-phase chemical for analysis; a piezoelectric fan to produce an air-flow through acoustic streaming to drive the gas-phase chemical released by the pre-concentration module to one or more downstream modules; an ionizer downstream from the piezoelectric fan to ionize the gas-phase chemical; and a gas sensor downstream from the piezoelectric fan and the ionizer to detect the ionized gas-phase chemical driven by the piezoelectric fan. The piezoelectric fan can include a stack of thin-film layers that includes a thin-film piezoelectric layer. The ion-gas sensor device is made into an ultra-portable package capable of integration with mobile communication devices, such as PDA devices or smart phones.

In yet another aspect, another ion-gas sensor device is disclosed. This ion-gas sensor device includes an integrated pre-concentration and ionization module that further includes a first material layer to collect and concentrate a gas-phase molecules for analysis and a second material layer underneath the first material layer to ionize the gas-phase molecules. The ion-gas sensor device also includes a piezoelectric fan to produce an air-flow through acoustic streaming to drive ionized gas-phase molecules released by the integrated pre-concentration and ionization module to one or more downstream modules. The ion-gas sensor device additionally includes a gas sensor downstream from the piezoelectric fan to detect the ionized gas-phase molecules driven by the piezoelectric fan. In some embodiments, the first material layer is a functionalized material for molecule collection and concentration and the second material layer is a $LiNbO_3$ crystal. The integrated pre-concentration and ionization module further includes a resistive heater placed underneath the second material layer. The heat generated by the resistive heater both triggers ionization of the gas-phase molecules adsorbed in the functionalized material by the ionization module and the ionized gas-phase molecules adsorbed in the functionalized material to be released from the functionalized material.

In yet another aspect, another ion-gas sensor device is disclosed. This ion-gas sensor device includes a pre-concentration module to collect and concentrate a gas-phase chemical for analysis; an integrated air pump and ionization module that includes a piezoelectric fan to produce an air-flow through acoustic streaming to drive the gas-phase chemical released by the pre-concentration module to one or more downstream modules. The piezoelectric fan includes a region configured to ionize the gas-phase chemical driven by the piezoelectric fan. This ion-gas sensor device also includes a gas sensor downstream from the integrated air pump and ionization module to detect the ionized gas-phase chemical driven by the piezoelectric fan. In some embodiments, the integrated air pump and ionization module includes a PZT high voltage transformer.

Microscale ion-mobility measurement is an approach to sensing gases in ultra-portable packages such as the burgeoning hand-held smart-phone markets. A key component of a gas sensor is the ability to sample the air molecules at rates determined by convection rather than diffusion for faster detection time. Embodiments of the disclosed technology include devices having a piezoelectric micro-fan, including a micro-fan architecture that is low power (e.g., 10.6 mW/sccm), low voltage (e.g., 8.5 V/sccm), and sufficiently small (0.1 $mm^3$/sccm). Embodiments of the disclosed technology includes also include various chip-size ionizers for gas analyte ionization. In some implementations, for example, the devices can include a multi-electrode configuration of ion-detection with less than 5V operating voltage. Exemplary implementations of the disclosed technology described herein demonstrate a pathway towards a chip-scale ion-mobility based gas detector with a process compatible with the ion-detection system, and the actuate and sense micro-fan architecture presented here.

FIG. 1 shows a block diagram of an exemplary chip scale gas sensor 100 of the disclosed technology. This chip scale gas sensor includes, in the order of the input side to the side, a pre-concentrator 102, a piezoelectric fan 104 for air pumping, an ionizer 106 for gas ionization, an ion-mobility spectrometry (IMS) gas sensor 108, and a data analyzer 110. In some embodiments, data analyzer 110 is not part of the chip scale gas sensor 100 and the chip scale gas sensor uses a processor of a mobile device for processing the data generated by IMS gas sensor 108. In some embodiments, the order of the piezoelectric fan 104 and the ionizer 106 can be switched. In some embodiments, the pre-concentrator 102 and the ionizer 106 are integrated and the integrated module can be placed before the piezoelectric fan 104. In other embodiments, the piezoelectric fan 104 and the ionizer 106 are integrated as a combined module. Furthermore, other orders of the modules shown in FIG. 1 and options for integrating these modules are possible. The basic functionalities of the illustrated modules of the chip scale gas sensor 100 are now described.

The pre-concentrator module performs the task of collecting volatile organic compounds (VOCs) or other gas analytes and concentrating these compounds before they are analyzed. For example, when the chip scale gas sensor is used as a breath sensor, the pre-concentrator collects VOCs during a regular phone call/electronic device usage over 2-3 minutes from the user's breath when the user talks. The module typically accumulates these compounds on a film layer that is functionalized for molecule collection and concentration. For analysis, the pre-concentrator is typically heated to release these molecules from the functionalized film. The heating system is typically considered a part of the pre-concentrator.

The piezoelectric fan or simply "piezo fan" is a module that transfers the collected gas compounds that are released by the heated pre-concentrator and transfers them using acoustic streaming (like a blowing fan) to the ionizer for ionization. The air-flow created by the piezo fan also drives the ionized gas analytes toward the IMS gas sensor. Various embodiments of the disclosed technology provide both a thin-film-based piezoelectric fan made by microfabrication and a bulk piezoelectric fan made by micro-machining.

The ionizer is a module that performs the task of ionizing the gas compounds blown by the fan, i.e., gaining or accepting electrons or ionic charges, prior to analysis by the IMS sensor. Various embodiments of the disclosed technology provide different ionizer designs which have chip-scale integration capabilities. For example, one disclosed ionizer design uses radioactive Ni-63 (also referred to as "hot nickel" or "hot Ni-63" hereinafter) which is natural electron-emitter and has stability in ionization up to 100 years corresponding to its lifetime. Another ionizer design is based on pyroelectricity (i.e., heating to produce large electric potential difference) of lithium niobate ($LiNbO_3$) that enables ionization of the compounds when the $LiNbO_3$ crystal is cycled to rapidly increase or decrease in temperature. Yes another ionizer design uses a bulk piezoelectric beam with electrodes patterned on the beam to produce large strain at the beam anchor to enable large electric fields across small gaps, which in turn produces ions.

IMS sensor is a module that detects the ionized compounds that are flown by the piezoelectric fan and uses the charge to mass ratio (i.e., ion mobility) of the compounds for identifying the compounds. Data analyzer is a computing module, implemented in software or hardware or both, for interpreting and analyzing the data that is collected from the IMS sensor.

Figure 2:
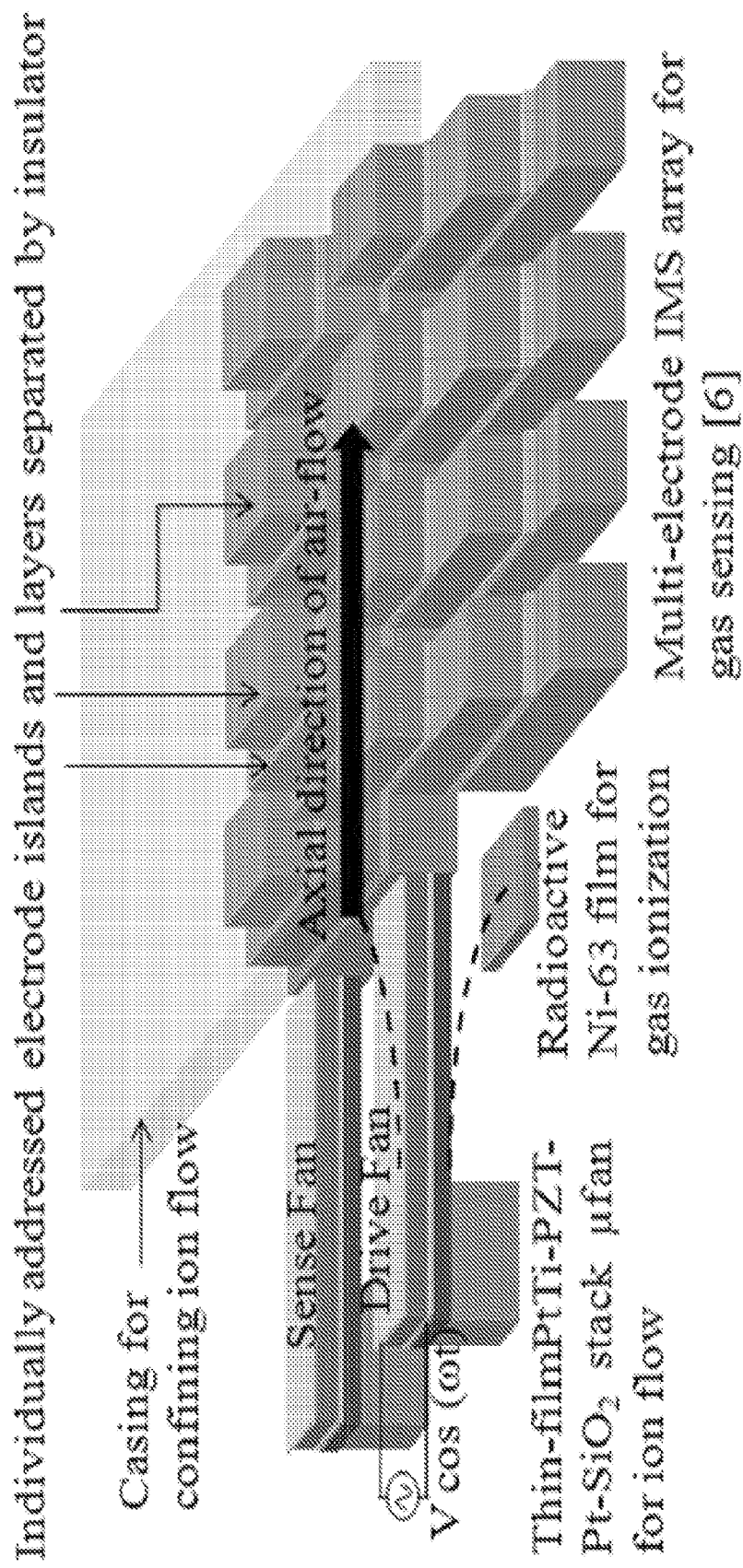
FIG. 2 shows a diagram of an exemplary chip scale ion-gas sensor of the disclosed technology that includes a piezoelectric sense-drive fan pair, a radioactive Ni-63 film for gas ionization, and an ion-mobility spectrometry (IMS) array gas sensor integrated as a package.

FIG. 2 shows a diagram of an exemplary chip scale ion-gas sensor of the disclosed technology that includes a piezoelectric sense-drive fan pair, a radioactive Ni-63 film for gas ionization, and an IMS array gas sensor integrated as a package. The modules depicted in FIG. 2 are described in more detail below.

Figures 3A, 3B, 3C, 3D:
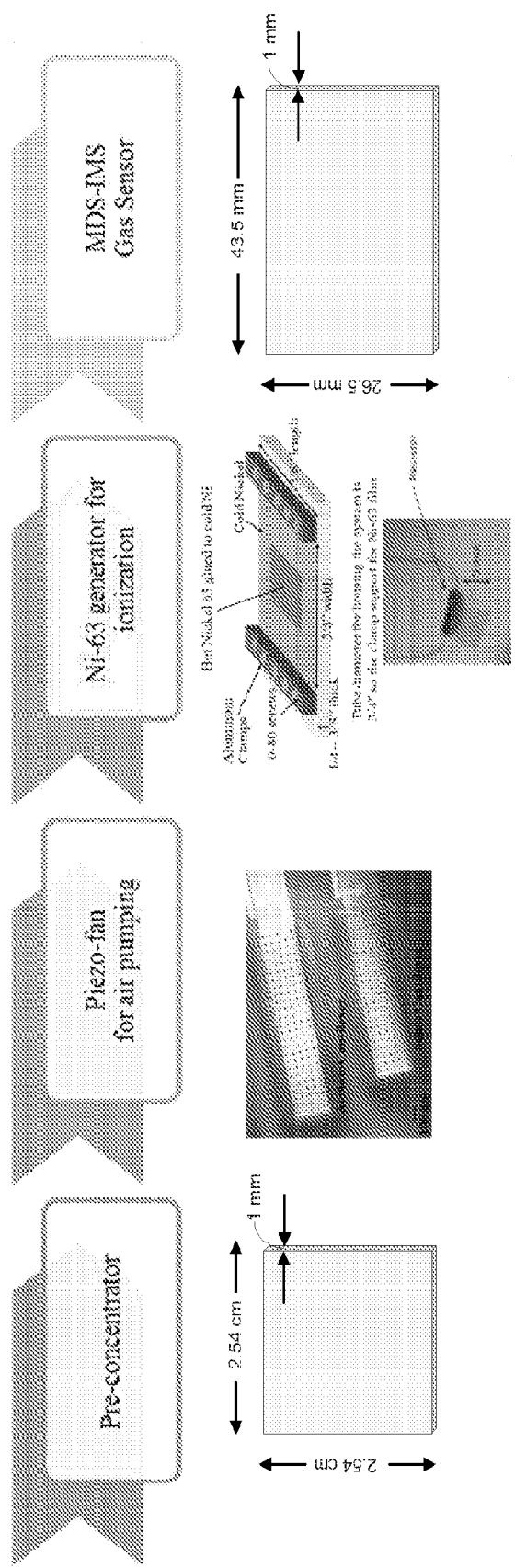
FIG. 3A shows exemplary dimensions of an exemplary micro pre-concentrator.
FIG. 3B shows exemplary dimensions of an exemplary piezoelectric fan.
FIG. 3C shows exemplary dimensions of an exemplary Ni-63 ionizer and an exemplary $LiNbO_3$ ionizer.
FIG. 3D shows exemplary dimensions of an exemplary IMS gas sensor.

For chip-size gas sensor integration, each module described above should have a chip size, as shown in FIG. 3A-FIG. 3D. FIG. 3A shows exemplary dimensions of an exemplary micro pre-concentrator. In this example, the overall dimensions of the micro pre-concentrator are 2.54 cm×2.54 cm×1 mm in which the active material dimensions are 5 mm×5 mm×350 µm. FIG. 3B shows exemplary dimensions of an exemplary piezoelectric fan. In this example, the overall dimensions of the piezo fan are 1 cm×1 cm×1.5 mm in which the active material dimensions are 1 mm×0.8 mm×0.5 µm. In another example, a more compact piezo fan has total dimensions of 5 mm×5 mm×500 µm. In other embodiments, the piezo fans used in the disclosed chip-size gas sensors have even smaller dimensions than the ones described above. FIG. 3C shows exemplary dimensions of an exemplary Ni-63 ionizer and an exemplary $LiNbO_3$ ionizer. In these examples, the overall dimensions of the Ni-63 and $LiNbO_3$ packages are 1.6 cm×1.6 cm×5 mm and 5 mm×5 mm×5 mm, respectively, in which the active dimensions are 1 cm×1 cm×100 um and 1 mm×1 mm×5 mm, respectively. In another example, a more compact ionizer has total dimensions of 5 mm×5 mm×2.5 mm. In other embodiments, the ionizers used in the disclosed chip-size gas sensors have even smaller dimensions than the ones described above. FIG. 3D shows exemplary dimensions of an exemplary IMS gas sensor. In this example, the overall dimensions of the gas sensor are 43.5 mm×26.5 mm×1 mm in which the separation and detection region dimensions are 20 mm×3 mm×30 µm. Based on the above exemplary dimensions of individual modules, an exemplary total package size of an exemplary chip-based gas sensor is ~3.5 cm×4.5 cm×5 mm, which is feasible for a PDA-based or smart phone-based portable gas-sensor. However, much smaller total package sizes of chip-based gas sensors can be implemented to be more compatible with PDAs and smart phones.

Figure 4:
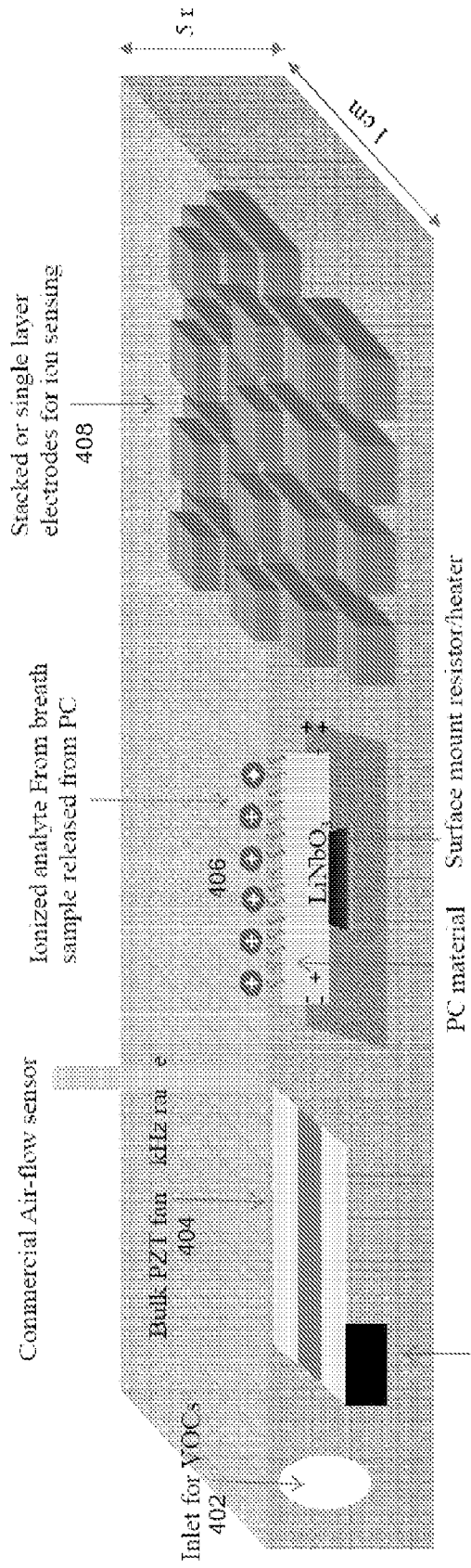
FIG. 4 shows a schematic of an exemplary bio-sniffing chip that includes various modules of an exemplary chip-scale gas sensor.

FIG. 4 shows a schematic of an exemplary bio-sniffing chip 400 that includes various modules of an exemplary chip-scale gas sensor. As can be seen from FIG. 4, bio-sniffing chip 400 includes an inlet 402 for receiving gas samples such as volatile organic compounds (VOCs) from a user's breath, which is located at one end of the bio-sniffing chip 400. Bio-sniffing chip 400 includes a bulk PZT fan 404 located immediately next to the inlet 402, and operating in the KHz range. However, bulk PZT fan 404 can be replaced with a thin-film PZT fan. Bio-sniffing chip 400 includes an integrated ionizer and pre-concentrator 406 located downstream from bulk PZT fan 404. More specifically, integrated ionizer and pre-concentrator 406 includes a $LiNbO_3$ ionizer comprising a $LiNbO_3$ crystal and a surface mount resistive heater, and a pre-concentration functionalized layer attached to the surface of the $LiNbO_3$ ionizer. The integration of the ionizer and the pre-concentrator has the benefit of significantly reducing power consumption of the overall chip-based gas sensor. However, other test chip configurations can use separate ionizer and pre-concentrator, and other types of ionizers. Bio-sniffing chip 400 also includes stacked or single layer electrode for ion sensing 408 which is located at the other end of bio-sniffing chip 400. In other gas-sensing chip configurations, the order of ionizer and fan can be switched. Using different configurations of the gas-sensing chips can facilitate identifying optimal ion-flow in order to avoid cold spots.

Piezoelectric Fan

In some embodiments of the disclosed technology, a thin-film piezoelectric-$SiO_2$ composite unimorph actuated at resonance is used as a fan (also referred to as a thin-film piezoelectric fan) to induce flow of the ions into a MDS-IMS device convectively by shedding vortices near the fan-tip. The micro-fan peak-to-peak displacement, magnified at resonance, produces air flow along its axis by shedding air vortices close to its tip, as well as re-circulating loops above surface of the fan. Devices based on thin-film piezoelectric fan are compatible with low-voltage (e.g., <5V) and low power platforms. Flow-rates of up to 7 cm/s have been measured with these devices. In some embodiments, when the thin-film piezoelectric fan operates at a higher flow-rates (referred to as the "drive fan"), another piezoelectric fan can be placed close to the drive fan to sense turbulent air-motion, and to provide a feedback signal for controlling the drive fan. The piezoelectric drive fan and the piezoelectric sense fan thus form a "piezoelectric drive-sense fan pair."

Figure 5:
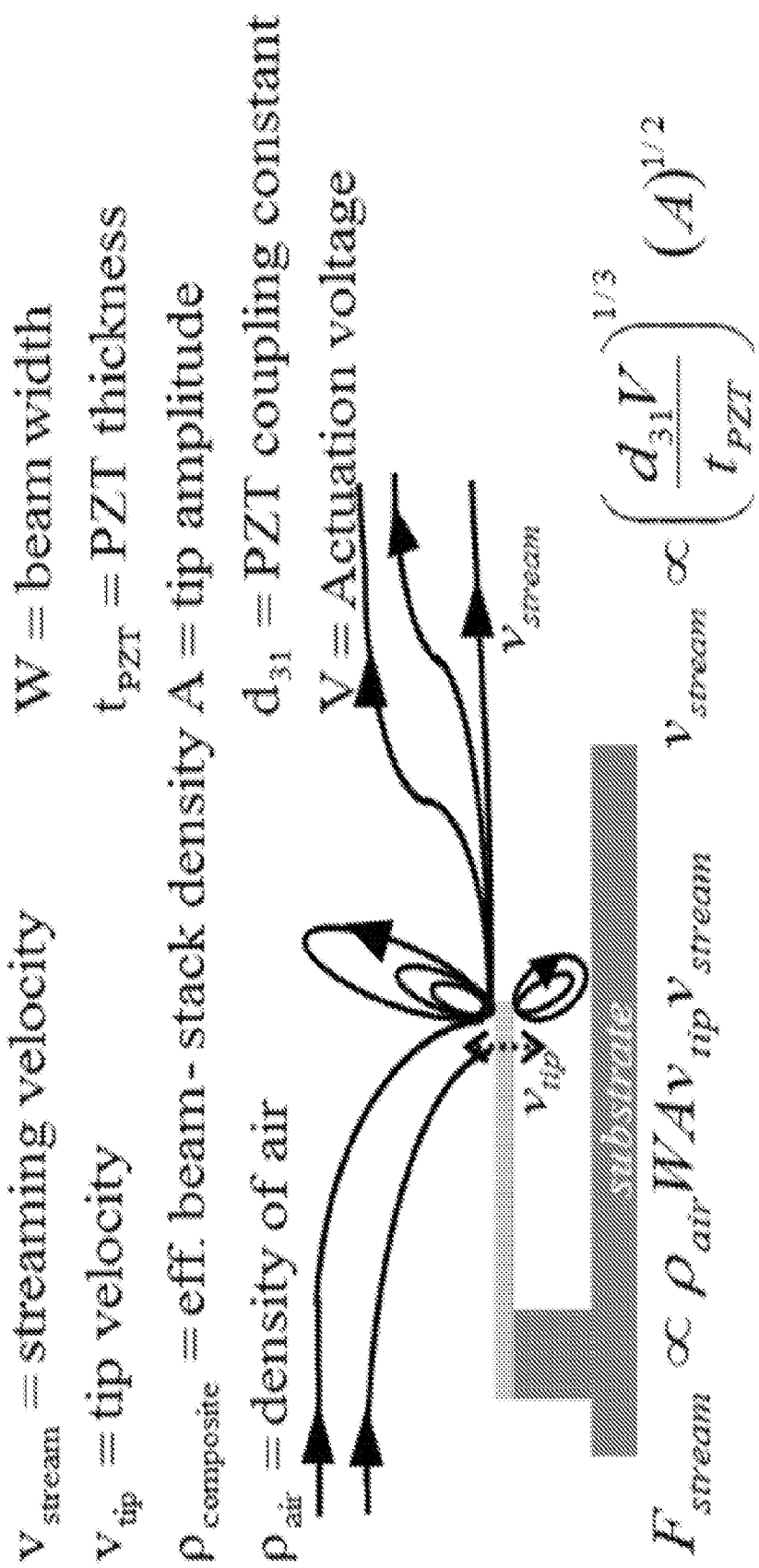
FIG. 5 shows exemplary streaming air-flow and re-circulating vortices above the tip of a piezoelectric fan and equations for air velocity and force as functions of devices parameters and constants.

FIG. 5 shows exemplary streaming air-flow and re-circulating vortices above the tip of a piezoelectric fan and equations for air velocity and force as functions of devices parameters and constants. The flow due to the piezoelectric fan is a function of Reynolds number of the resulting flow. The Reynolds number is a function of the tip-substrate gap, and etch-holes on the surface of the fan. The channel can be designed to achieve a desired flow that can be used in micro channels compatible with small form factors presented in hand-held electronic information devices. In FIG. 5, $F_{stream}$ is the streaming force for driving ions into the IMS device, and $v_{stream}$ is the velocity of ions being streamed.

Multilayer analysis for arbitrary piezoelectric-elastic layer stacks, and exemplary measured data from DC actuation from 0-6V, yielded piezoelectric coupling coefficient $d_{31}=-85.8\pm5$ pC/N for the PZT films, less than the values for bulk PZT but within expectation for multi-layer stressed thin-film devices. Resonance frequencies were measured to be at 614 Hz and 505 Hz, with peak-to-peak tip-displacement >200 um 2-Vpp, with 2.5 mW power input. A RTD element was used to measure air-velocity close to the tip of the fan.

Table 1 compares piezoelectric fan designs with conventional fan designs.

TABLE 1

Comparing piezoelectric fan designs with conventional fan designs

| Work | Max Flow (µL/min) | Nominal Voltage | Power (mW) |
|---|---|---|---|
| Conventional Micropump | 4000 | 100 V | ~57 |
| Conventional Electrostatic Microfan | 10 | 100 $V_{p-p}$ | — |
| Exemplary Piezofan of Disclosed Tech | 235.6 | 2 $V_{p-p}$ | 2.5 |

Figure 6:
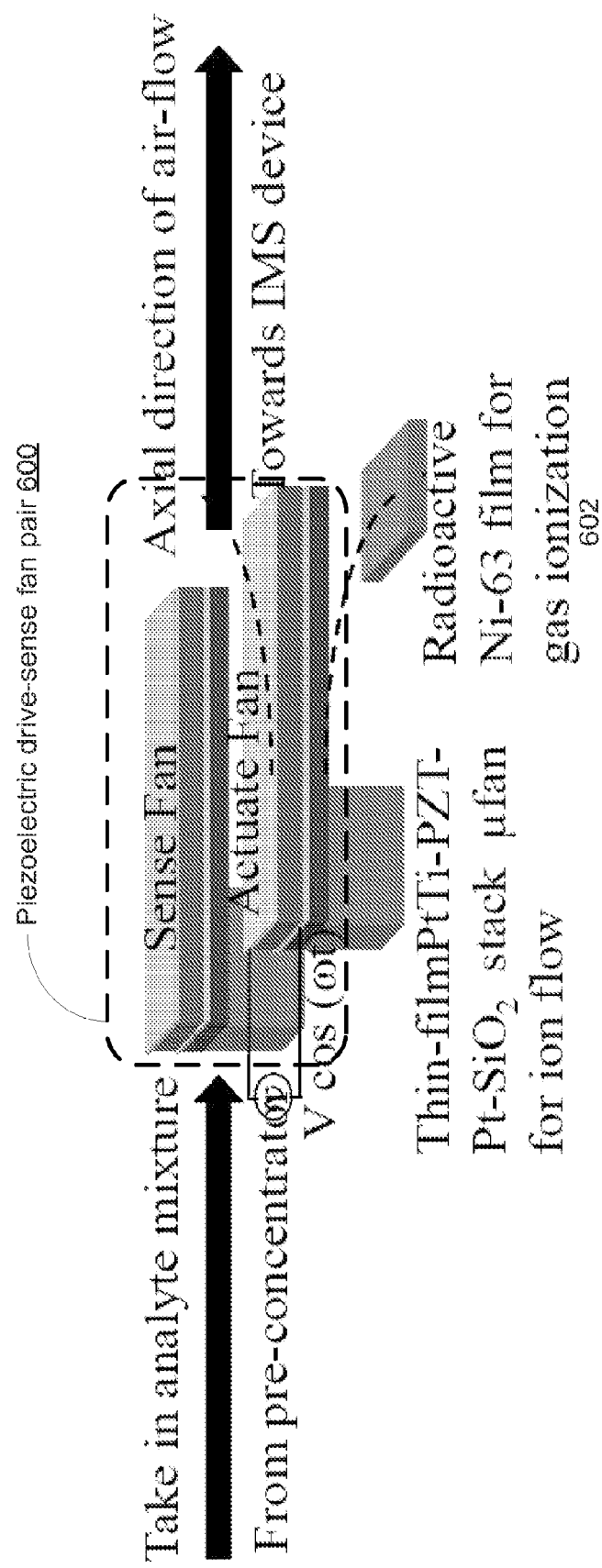
FIG. 6 shows an exemplary gas sensing device including a piezoelectric drive-sense fan pair for generating an air-flow within the gas sensing device.

FIG. 6 shows an exemplary gas sensing device including a piezoelectric drive-sense fan pair 600 for generating an air-flow within the gas sensing device. In the proposed gas sensing device, piezoelectric drive-sense fan pair 600 for air-flow generation, and the radioactive Ni-63 film 602 for gas ionization are preceded by the pre-concentrator (not shown).

As can be seen in FIG. 6, the drive fan or the "actuate fan" of drive-sense fan pair 600 actuated at resonance produces a large amplitude tip vibration to enable mechanical power-transfer to drive an analyte mixture from the pre-concentrator toward an IMS device. The sense fan of drive-sense fan pair 600 next to the drive fan measures a lateral turbulent air-motion to provide feedback signal for controlling the drive signal (e.g., V cos (ωt)) of the drive fan XXX. FIG. 6 also shows radioactive Ni-63 film 602 placed directly under the vibrating tip of the actuate fan. Ni-63 film 602 includes high-energy density radioactive electron-emitting Ni-63 which is capable of causing broadband ionization of the analytes. In some embodiments, Ni-63 film 602 emits primary and secondary electrons to produce ~nA of ionization current. By combining the fan module and the ionization module, the disclosed biosensing device can potentially reduce bio-sensing time from ~100 seconds to <0.1 second compared to the diffusion-limited sensing techniques.

Although gas sensing device shown in FIG. 6 has the fan module precedes the ionization module, in other embodiments the order of the fan and ionization modules can be switched so that the ionization process is carried out immediately after the pre-concentrator.

Figure 7:
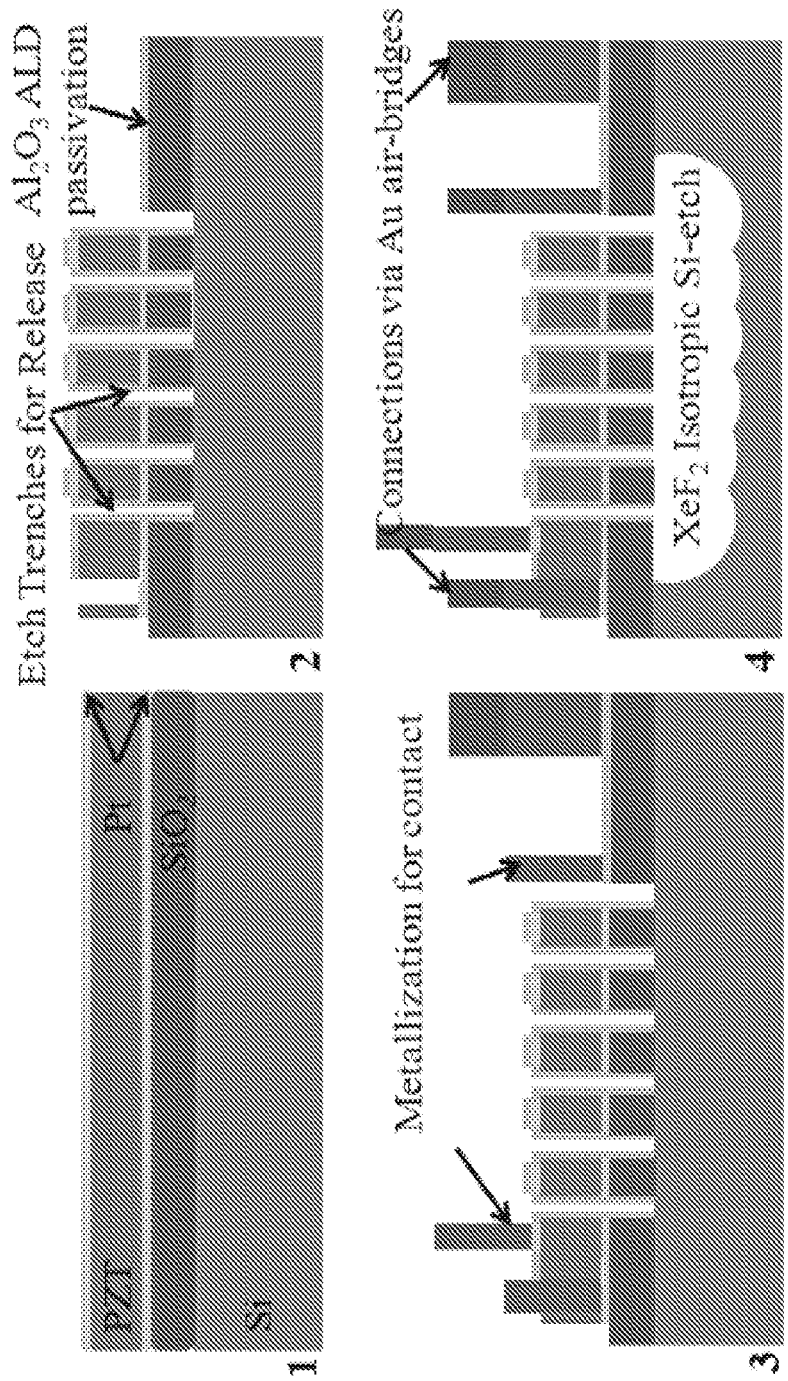
FIG. 7 shows an exemplary process of fabricating a thin-film-based piezoelectric fan.

FIG. 7 shows an exemplary process of fabricating a thin-film-based piezoelectric fan. As shown in subplot 1 of FIG. 7, the process may start with a Si substrate and then deposit a stack of layers, such as a $SiO_2$—Pt-PZT-Pt stack. The $SiO_2$ oxide layer may be formed by thermal deposition/growth. The PZT layer can be formed by spinning of PZT material. Next, as shown in subplot 2 of FIG. 7, photolithograph steps are applied to the PZT stack for etching and patterning various layers. These photolithograph steps include coating a $Al_2O_3$ ALD passivation layer as masks for etching and patterning of various layers. As shown in subplot 2, the etching process forms trenches in the PZT stack for structure release in later steps. Next, as shown in subplot 3 of FIG. 7, a metallization step through evaporation is applied to the PZT structure to form electrical contacts.

Next, as shown in subplot 4 of FIG. 7, a $XeF_2$ etching is performed on the Si substrate to undercut and release the thin-film piezoelectric fan structure. Also, electrical connections are formed to interconnect the electrical contacts, for example, by using Au air-bridges.

Figure 8:
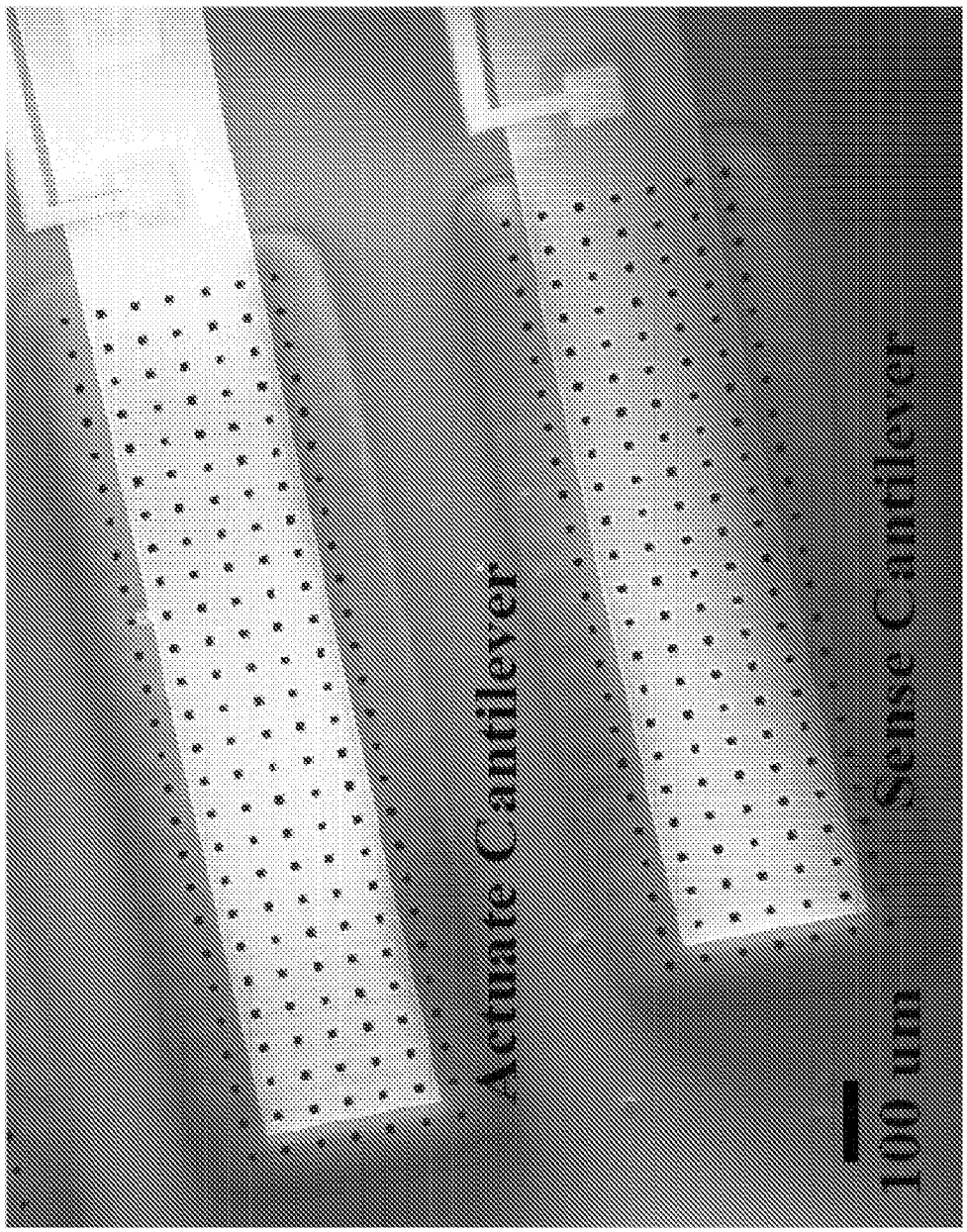
FIG. 8 shows an SEM image of an exemplary piezoelectric actuate-sense fan pair fabricated using the PZT process described in FIG. 7.

FIG. 8 shows an SEM image of an exemplary piezoelectric actuate-sense fan pair fabricated using the PZT process described in FIG. 7.

Figure 9:
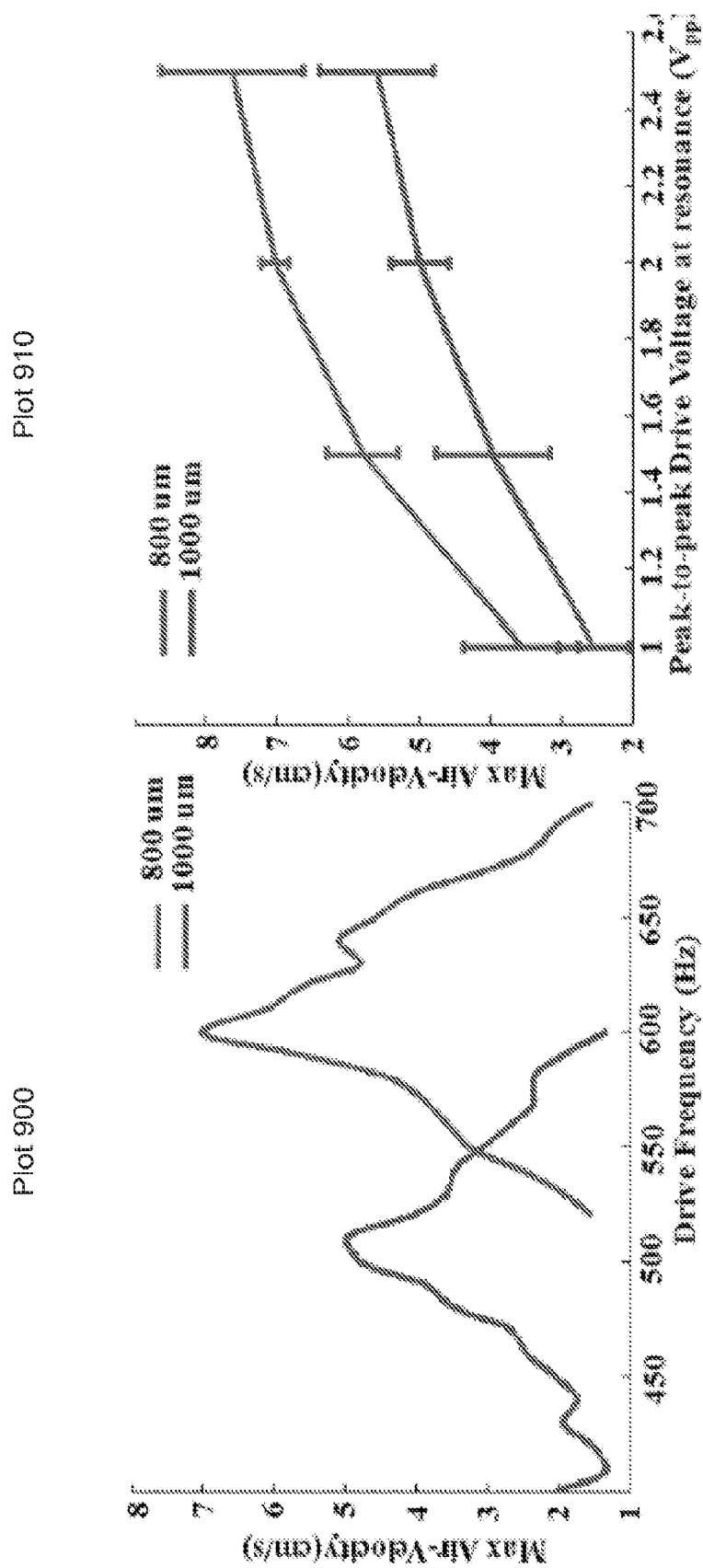
FIG. 9 shows measured maximum air-velocity at the tip of an exemplary actuate fan by using a resistance temperature detector sensor close to the tip of the actuate fan.

Exemplary implementations of the exemplary devices were performed. The exemplary piezoelectric actuate-sense fan pairs with widths of 200 µm and lengths 800 µm and 1000 µm, respectively, were tested in micro-channels. FIG. 9 shows measured maximum air-velocity at the tip of an exemplary actuate fan by using a RTD sensor close to the tip of the actuate fan. More specifically, the left data plot 900 shows maximum air-velocity as a function of drive frequency on the PZT fan, and the right data plot 910 shows maximum air-velocity as a function of drive voltage at resonance. The maximum air-velocity measured at the tip of the piezoelectric fan is ~7 cm/sec. The maximum air-velocity vs. drive voltage data demonstrate the compatibility of such PZT fan for low-voltage platforms.

Figure 10:
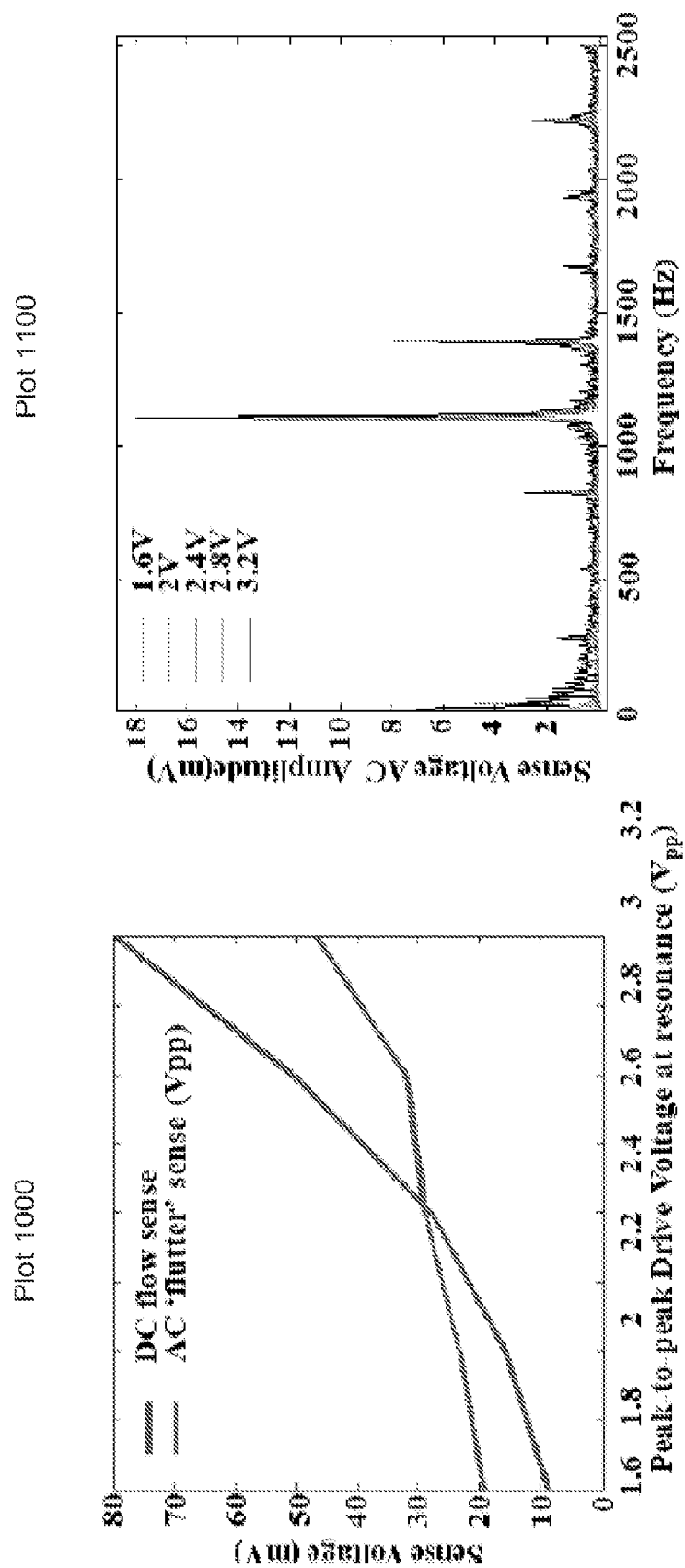
FIG. 10 shows the measured DC and AC sense voltages from an exemplary sense fan to provide an integrated feedback for the piezoelectric sense-actuate fan pair.

FIG. 10 shows the measured DC and AC sense voltages from an exemplary sense fan to provide an integrated feedback for the piezoelectric actuate-sense fan pair. For example, the left plot 1000 in FIG. 10 shows that the DC and AC sense voltages are produced due to the reverse piezoelectric effect as a result of lateral air-motion forces. The right plot 1010 in FIG. 10 shows a spectrum of AC sense voltage showing AC sense at twice of the drive frequency. The larger random-motion AC signal from the flow indicates a critical flow where the sense fan becomes unstable and starts to flutter, allowing the monitoring of the Reynolds number.

Table 2 shows exemplary results of fan frequency and displacement analysis for both thin-film PZT fan and bulk PZT fan. The analysis for bulk PZT is performed with data measured from laser Doppler vibrometer (LDV) in-plane strobing measurements. The results indicate a very low quality (Q)-factor for the bulk PZT fan structure. In contrast, thin-film PZT fans displays very higher Q-factor that approaches material limited performance. Also, much higher tip-velocity and an integrated fan motion reaching 40 cm/sec have been achieved. In some exemplary thin-film PZT fans, tip velocity >1 msec has been measured.

TABLE 2

Fan Performance Analysis (comparing thin film PZT fan with bulk PZT fan)

| Fan | Res. Frequency | Displacement at resonance | Tip Velocity |
|---|---|---|---|
| Thin film | 500-600 Hz | 140-200 um | 62.8 cm/sec |
| Bulk | 20 kHz | 300 nm (from strobing) | 3.78 cm/sec (low Q) |

Figure 11:
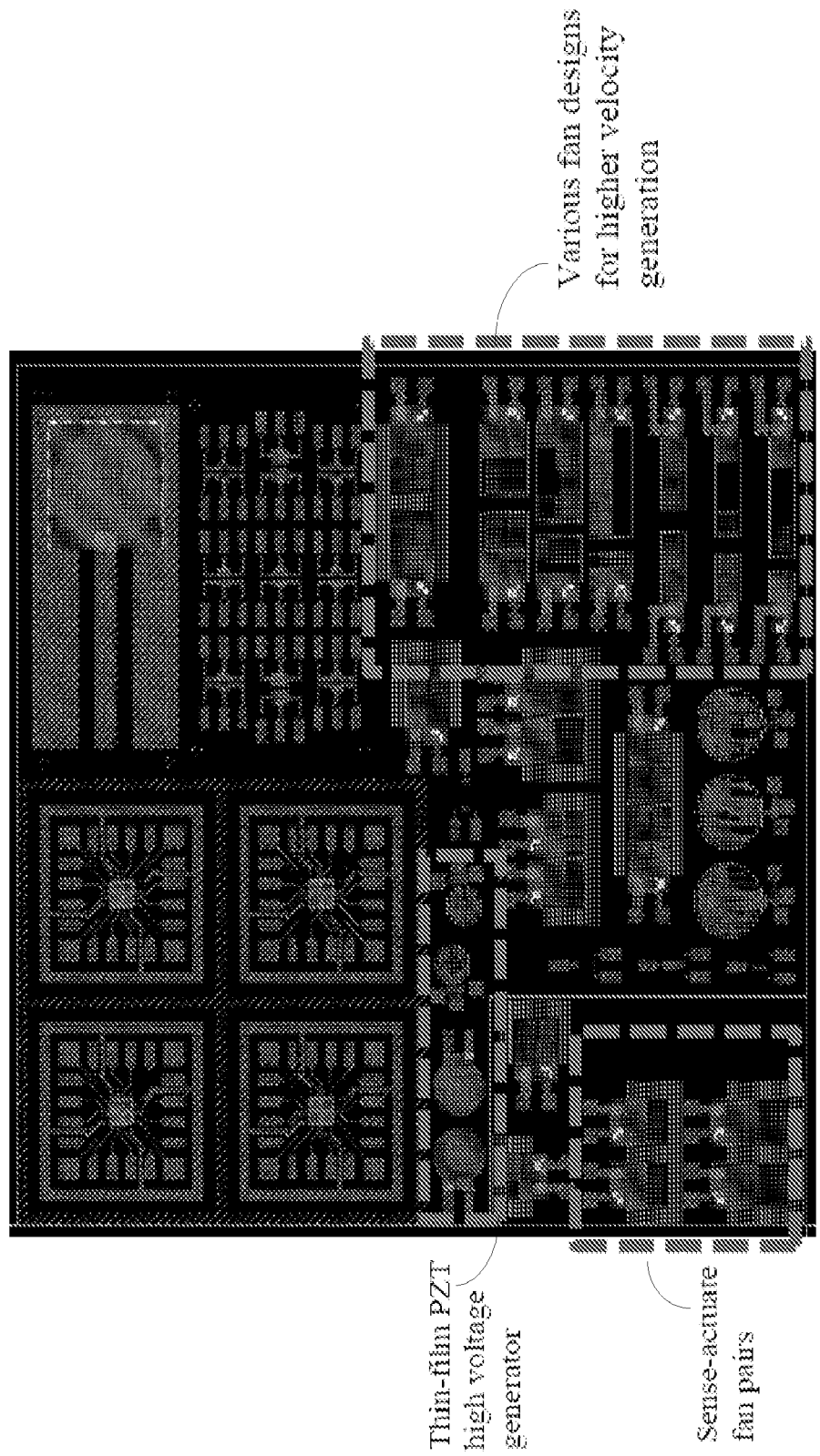
FIG. 11 shows exemplary tape-out designs for various fans for higher velocity generation, sense-actuate fan pairs and thin-film high voltage transformers.

FIG. 11 shows exemplary designs for various fans for higher velocity generation, sense-actuate fan pairs and thin-film high voltage transformers. These designs were created to evaluate performance of piezo-fans and sense-actuate fan pairs over a broad range of devices. The bottom left devices show sense-actuate fan pairs with a broad range of frequencies, with identical sense fan and actuate fan in each pair. The bottom right devices are fans for producing air-flow without any feedback but covering a wide range of frequencies for enhanced flow-rate production for driving ions into the IMS device. The top left corner shows implementations of PZT transformers for high-voltage generation using thin-film PZT.

Ni-63 Ionizer

Figure 12B:
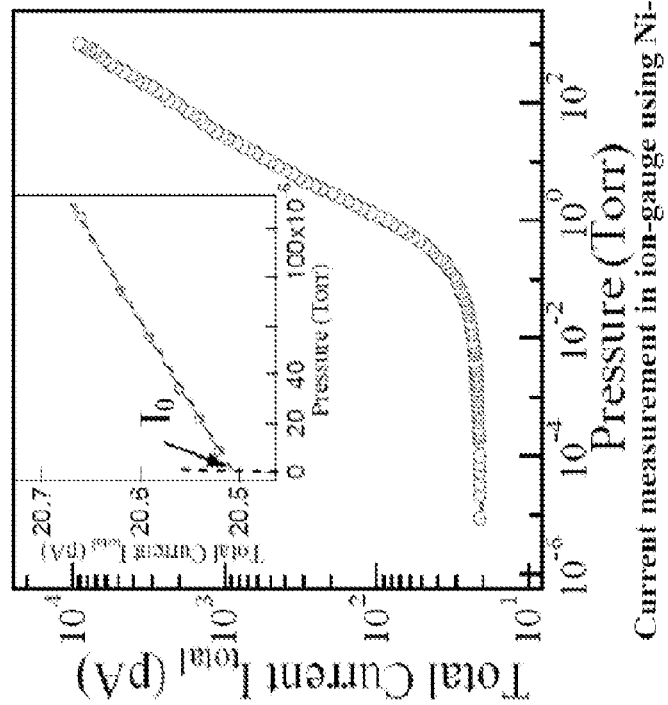
FIG. 12B shows current measurement in an ion-gauge using radioactive Ni-63.
Figure 12A:
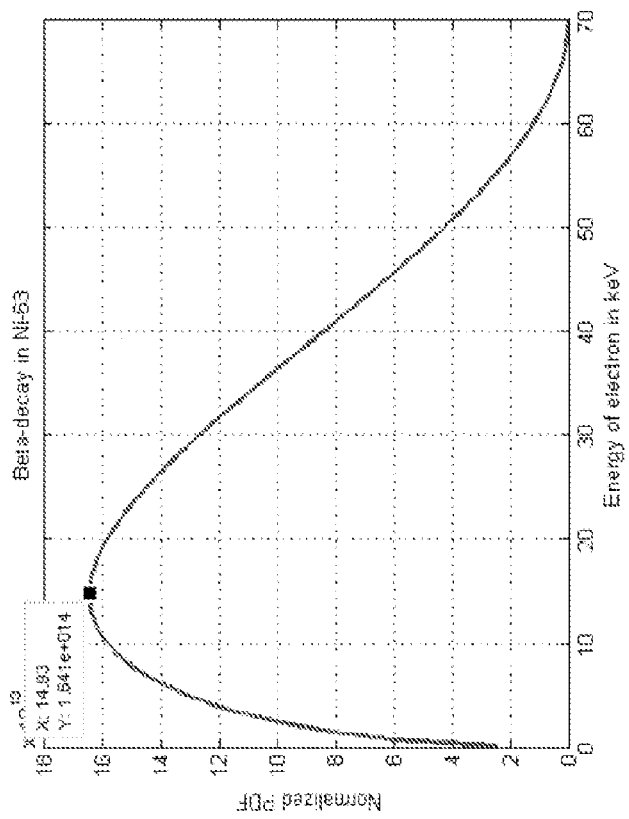
FIG. 12A shows energy distribution of emitted primary electrons from radioactive Ni-63 (hot Ni-63).

Ni-63 is an electron-emitting radioactive material with a high-energy density, yet benign in terms of penetrating power. Ni-63 can also be electro-plated in thin films. The half-life of Ni-63 is 100 years and it is capable of producing primary electrons of energies 0-70 keV with average energy =17 keV. A 1 mm×1 mm Ni-63 film has an activity of ~100 µCurie or $3.7 \times 10^6$ disintegrations per second with average energy of 17 keV and low cross-section of ionization. When accelerated across a potential difference, the primary electrons strike metal electrodes producing secondary electrons with energies ~0-300 eV, which is sufficient to overcome the first ionization energies of most compounds. FIG. 12A shows energy distribution of emitted primary electrons from Ni-63. FIG. 12B shows current measurement in an ion-gauge using Ni-63.

Figure 13:
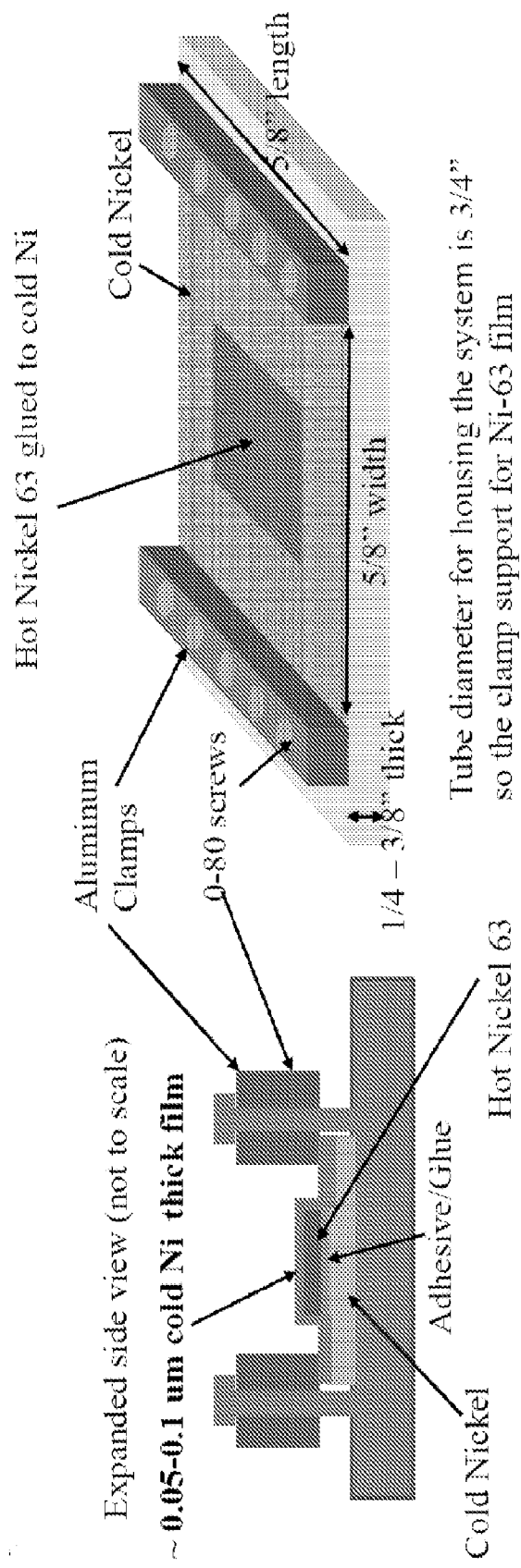
FIG. 13 shows an example of using a cold Ni/hot Ni-63 compound as an ionization module.

Radioactive Ni-63 by itself may not be ideal for handling, processing or direct use in ionization. Care must be taken to avoid contamination and flaking during handling of hot Ni-63 to avoid long term radioactive contamination of any kind or health damage. However, electro-plating cold Ni on top of hot Ni-63 and using the structure as a component for ionization allows for much safer handling. FIG. 13 shows an example of using a cold Ni/hot Ni-63 compound as an ionization module. As can be seen in FIG. 13, a cold Ni layer is electro-plated on a substrate and then hot Ni-63 can be adhered/glued to the cold Ni layer. A very thin cold Ni film can be coated over the hot Ni-63. The whole module can be clamped down with aluminum clamps.

Figure 14:
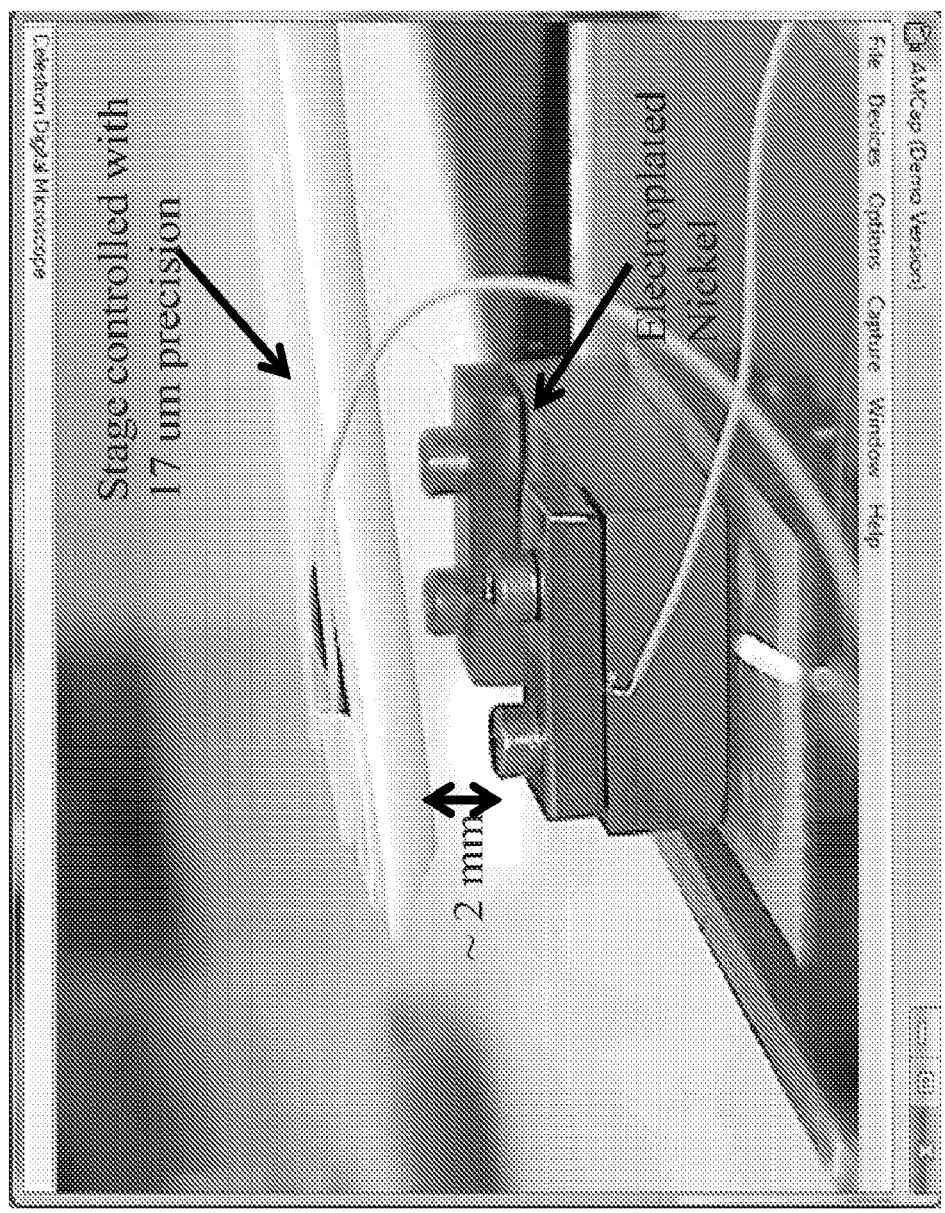
FIG. 14 shows an optical image of a physical setup for measuring current vs. bias voltage (IV) and for measuring current vs. test electrode distance to the Ni-film (IZ, i.e., current versus gap Z) of a Ni-63 ionizer.
Figure 15:
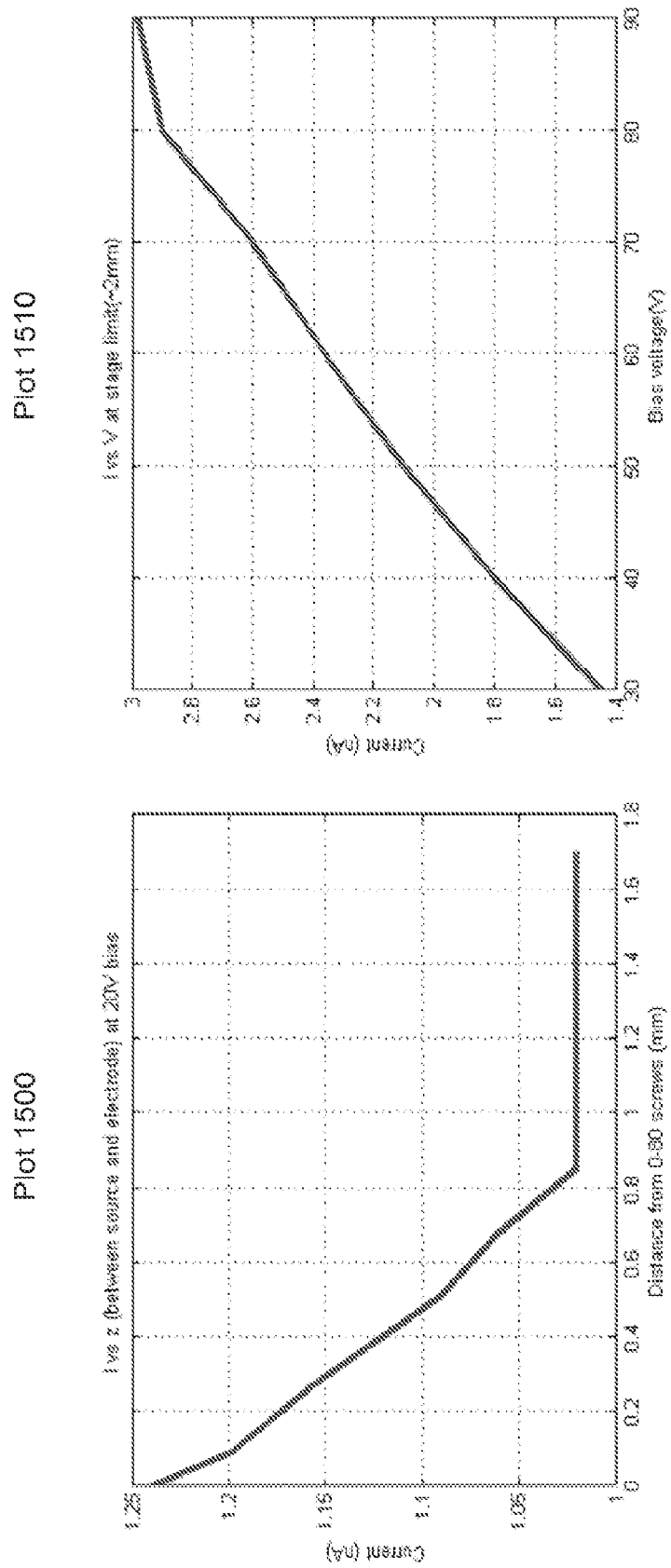
FIG. 15 shows exemplary results of IZ measurements (left plot) and IV measurements (right plot) of an exemplary Ni-63 ionizer using the physical setup shown in FIG. 14.

FIG. 14 shows an optical image of a physical setup for measuring current vs. bias voltage (IV) and for measuring current vs. test electrode distance to the Ni-film (IZ, i.e., current versus gap Z) of a Ni-63 ionizer. FIG. 15 shows exemplary results of IZ measurements (left plot 1500) and IV measurements (right plot 1510) of an exemplary Ni-63 ionizer using the physical setup shown in FIG. 14. The currents shown in FIG. 15 are obtained with no bias voltage between the electrode and Ni-film. As can be seen in IZ measurement of FIG. 15, 110 pA of current is measured when the electrode is flush on 0-80 screws, and 70-80 pA of current is measured when the electrode is at stage limit (i.e., the maximum distance from Ni film). The results show large variation in current which can be due to film-electrode misalignment and copper electrode is not exactly flush on the stage.

FIG. 16 shows exemplary results of IV measurements (left plot 1600) and IZ measurements (right plot 1610) of an exemplary Ni-63 ionizer using the test setup shown in FIG. 14. In the IV measurement, the blue curve corresponds to when the electrode is flush on 0-80 screws and the red curve corresponds to when the electrode is at stage limit. The results show more stable current partially because, compared to the measurements setup to obtain the results in FIG. 15, the copper electrode is better aligned to obtain the results in FIG. 16.

Figure 17:
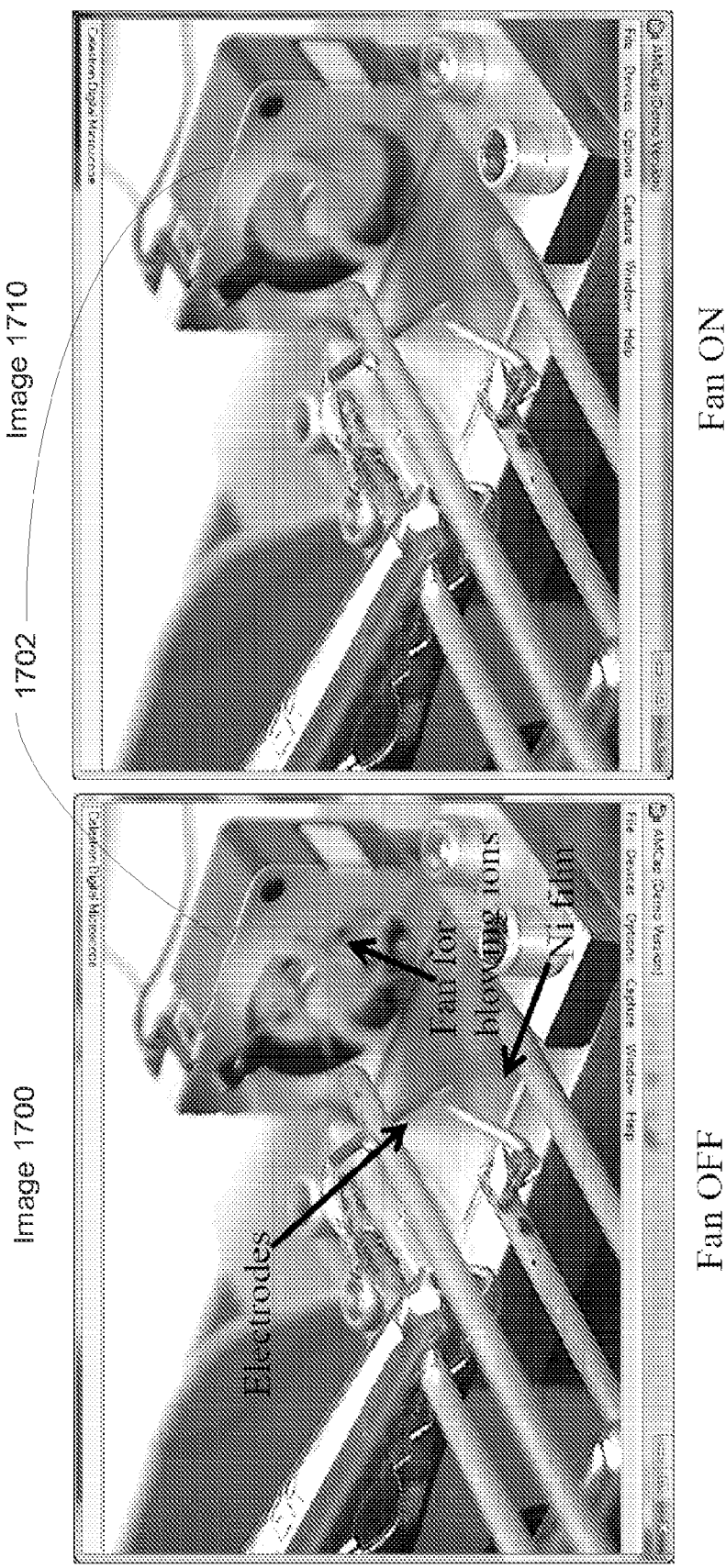
FIG. 17 shows optical images of an exemplary setup for measuring ionization current with a bias applied across electrodes and a fan for blowing ionized air.
Figure 18:
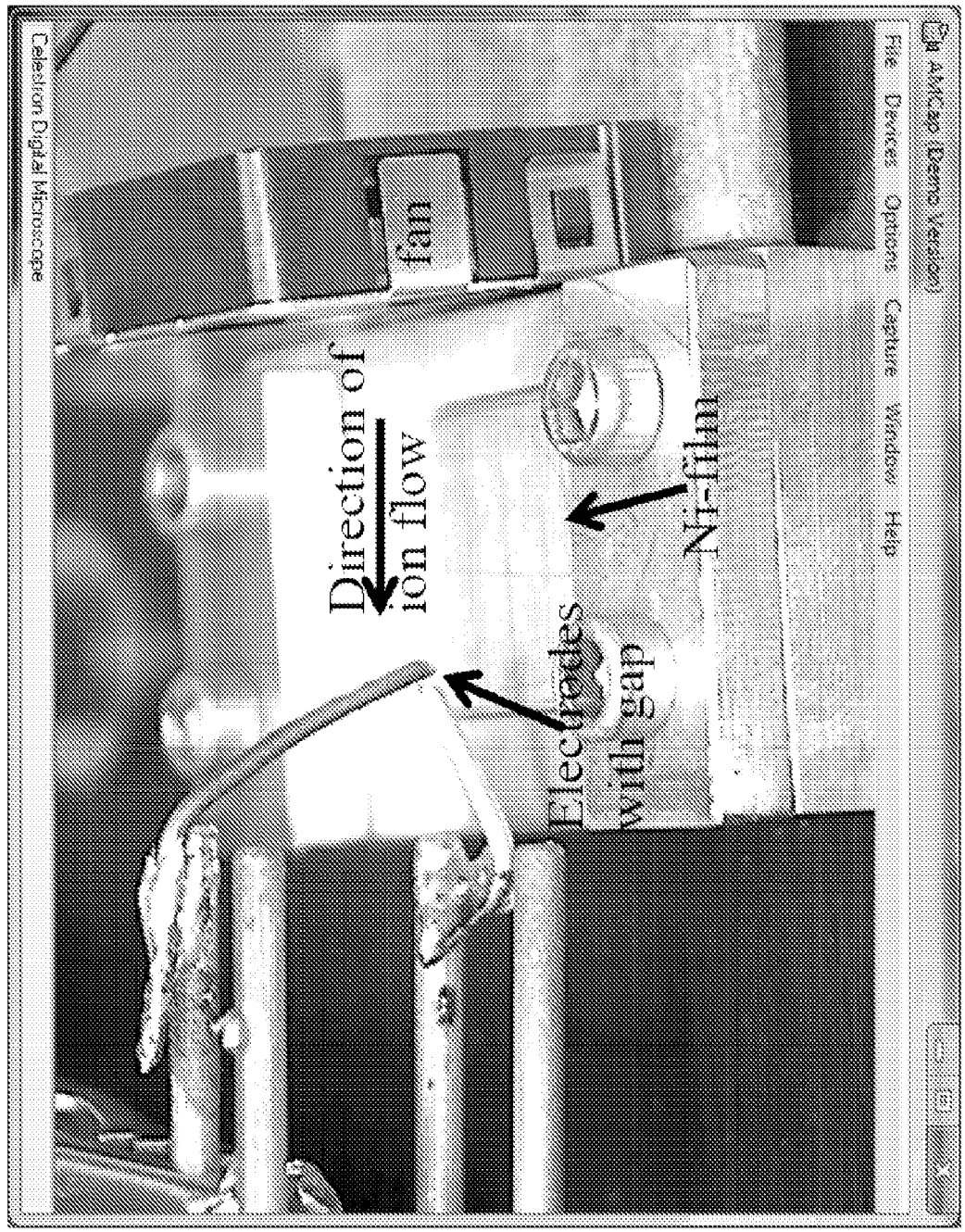
FIG. 18 shows another image at a different angle of the same test setup shown in FIG. 17 for measuring ionization current with a bias applied across electrodes.

FIG. 17 shows optical images of an exemplary setup for measuring ionization current with a bias applied across electrodes and a fan for blowing ionized air. As can be seen, a rotary fan 1702 is used in the test setup to blow ionized air towards electrodes, which are varied at different distances from the Ni film. The left image 1700 in FIG. 17 shows when the fan 1702 is turned off and the right image 1710 shows when the fan 1702 is turned on. FIG. 18 shows another image at a different angle of the same setup shown in FIG. 17 for measuring ionization current with a bias applied across electrodes. No significant difference was observed in measured ionization current when the fan 1702 is turned on and when it is turned off. This result can be due to that the rotary fan used in these measurements does not produce large flow rates and the bulk electrodes are not optimized for testing. There is also lack of a stage capable of fine control of electrode placement relative to the Ni film. Hence, there is a need to replace the rotary fan with a piezoelectric micro-fan and to replace the bulk electrodes with microfabricated electrodes.

Lithium Niobate LiNbO$_3$) Ionizer

Alternatively to using Ni-63 ionizer, a Lithium Niobate (LiNbO$_3$) pyroelectric ionization technique uses Z-cut LiNbO$_3$ crystal with an attached resistive heater attached to the crystal. For example, the heater can be implemented using a 68 ohm, 0.5-W resistor, epoxied to the LiNbO$_3$ with a commercial thermal adhesive on +z plate of the LiNbO$_3$ crystal. When used in an ionization setup, the Z-plate of the crystal is exposed to the ambient air for ionization. The resistor is heated with Joule heating to cause crystal temperature to increase.

Potential difference created in the LiNbO$_3$ crystal can be measured as a function of increase in temperature ($\Delta T$):

$$V = \frac{d_{cr}\phi(\Delta T)}{\varepsilon_{cr}}$$

wherein $d_{cr}$ is distance between the two plates, $\phi$ is the pyroelectric constant, and $\varepsilon_{cr}$ is the dielectric constant.

Figure 19:
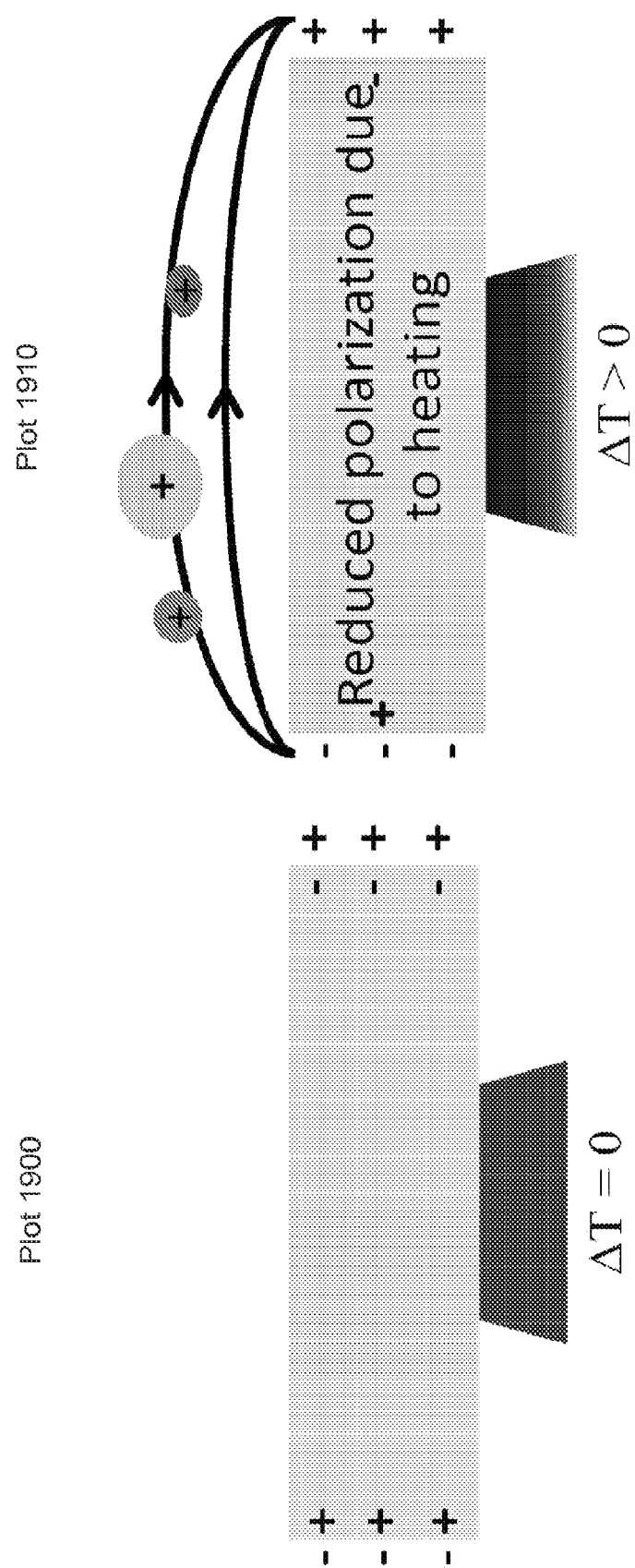
FIG. 19 shows conceptual diagrams of a Z-cut $LiNbO_3$ crystal with (right plot) and without (left plot) heating.

FIG. 19 shows conceptual diagrams of a Z-cut LiNbO$_3$ crystal with (right plot 1910) and without (left plot 1900) heating. As can be seen in FIG. XX, when Z-cut LiNbO$_3$ crystal is not heated (i.e., $\Delta T=0$), positive and negative charges in the crystal distribute evenly to neutralize each other. When the crystal is heated (i.e., $\Delta T>0$), positive and negative charges redistribute to cause a potential difference across the crystal. LiNbO$_3$ crystal can be a better ionizer candidate than PZT material for ionization because the intrinsic pyroelectric coefficient of a LiNbO$_3$ crystal is much higher than that can be tailored for pyroelectric PZT (e.g., it's ~3-5 µC/m$^2$K for PZT materials vs.70-100 µC/m$^2$K for LiNbO$_3$). Moreover, the dielectric constant is much lower in LiNbO$_3$ crystal at 46$_{\varepsilon_0}$ compared 1100$_{\varepsilon_0}$ for PZT. Hence it is typically more convenient to obtain higher voltages with lithium niobate compared to PZT. However, with sufficiently long length of PZT and heating, ionization can also be implemented with PZT materials.

Figure 20A:
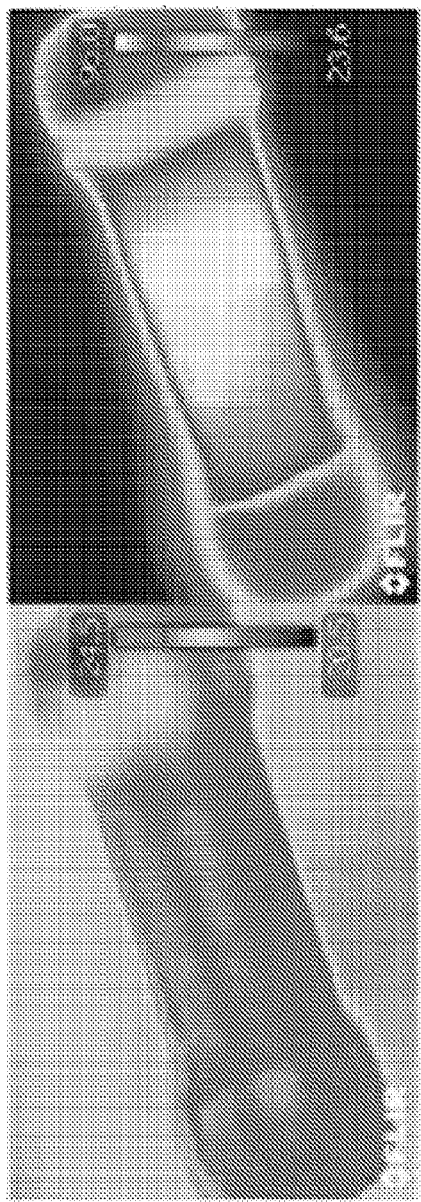
FIG. 20A shows infrared (IR) camera images of temperature profiles of a resistive heater without an voltage applied across the resistor (left image) and with a 5V voltage applied across the resistor (right image).
Figure 20B:
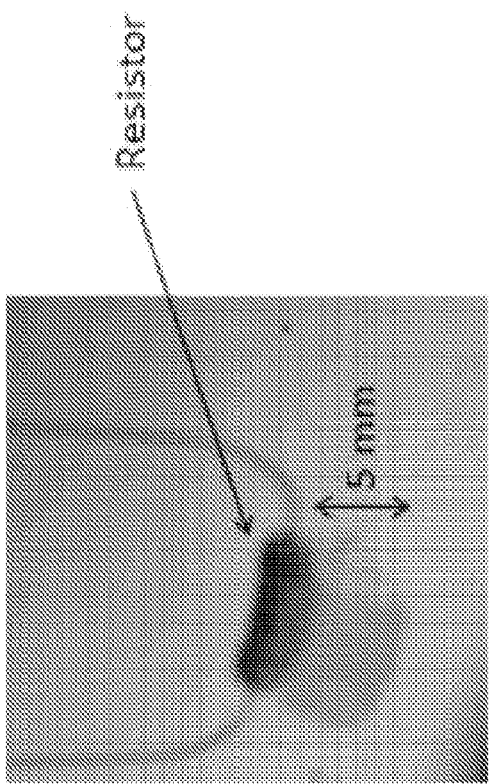
FIG. 20B show an exemplary assembly of a $LiNbO_3$ ionizer crystal with heater attached to the back of the crystal.

FIG. 20A shows infrared (IR) camera images of temperature profiles of a resistive heater without an voltage applied across the resistor (left image) and with a 5V voltage applied across the resistor (right image). FIG. 20B show an exemplary assembly of a LiNbO$_3$ ionizer crystal with heater attached to the back of the crystal.

Piezo-Transformers (PT) Ionizer

It is known that continuous stable emission of ions can be obtained at the surface of a PZT material using dielectric barrier discharge (DBD). While poling PZT along two different axes is not usually suited for planar surface and bulk micromachining, it is compatible with conventional thin-film as well as bulk deposition and etching techniques. It is desirable to create the same discharge using in-plane PZT disk-transformers which perform the task of amplifying the voltage and producing high electric field for ionization across small gaps. FIG. 21 shows light patterns of DBD at the surface of a piezo-transformer (PT) 1 minute after the onset of discharge (left image 2100) and after continuous stable discharge (right image 2110).

Figure 22:
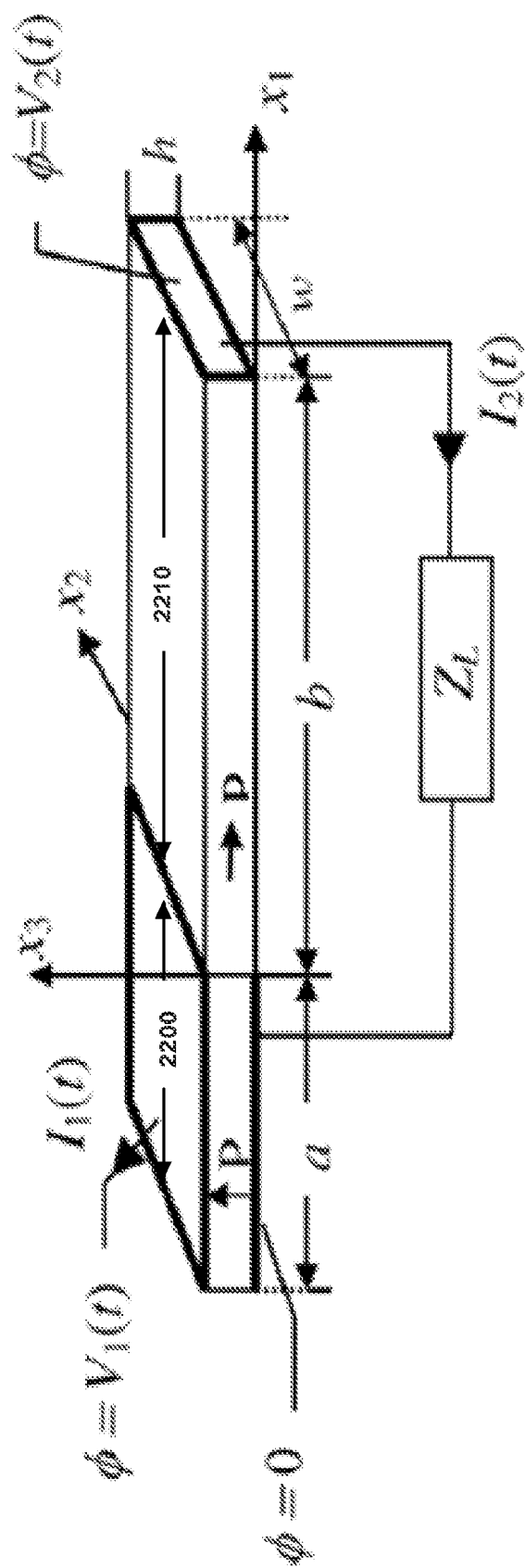
FIG. 22 shows a PZT poled along two different axes within the same material.

Rosen PZT transformers is well-known type of PT which can be used for computer backlights, portable electronic chargers, among other applications. FIG. 22 shows a PZT poled along two different axes within the same material. As can be seen in FIG. 22, the voltage is applied across the thickness of the PZT plate with the segment on the left section 2200 of the plate poled in the thickness direction. This voltage excites the resonant mode of the PZT plate to create a strain wave on the other section 2210 of the plate on the right. In section 2210, the poling is realized along the length of the PZT plate. The much longer length section 2210 versus the thickness section 2200 of the resonator gives rise to a higher voltage giving by the ratio of the length of section 2210 to the thickness of the plate. Although poled PZT materials have been used as bulk PZT transformers, such materials have not been used for micro-scale devices and systems.

Figure 23:
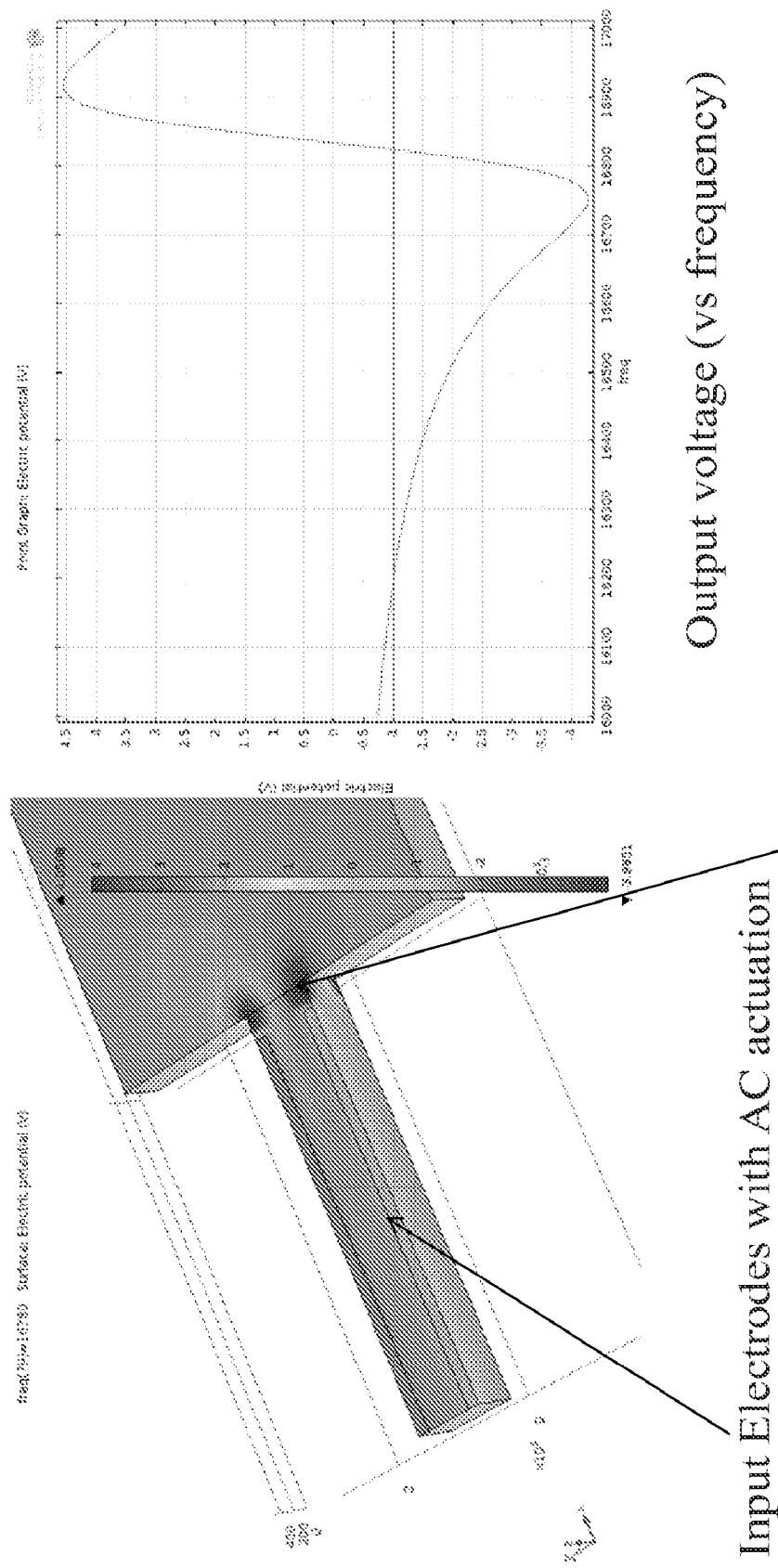
FIG. 23 shows simulation results of bimorph piezo-transformer (PT) operation.

FIG. 23 shows simulation results of bimorph piezo-transformer (PT) operation. As can be seen in FIG. 23, the input or drive electrodes of the bimorph PT receives AC actuation signals and the device concentrates driving energy from the AC actuation signals into the output electrode to produce high voltages. FIG. 24 shows COMSOL simulation results for sense-voltage produced (single-ended) with 1V AC signal applied to the drive electrodes for 450 um (left plot 2400) and 900 um (right plot 2410) wide PT beams. An isotropic loss factor of ~0.01 is assumed for these simulations.

Figure 25:
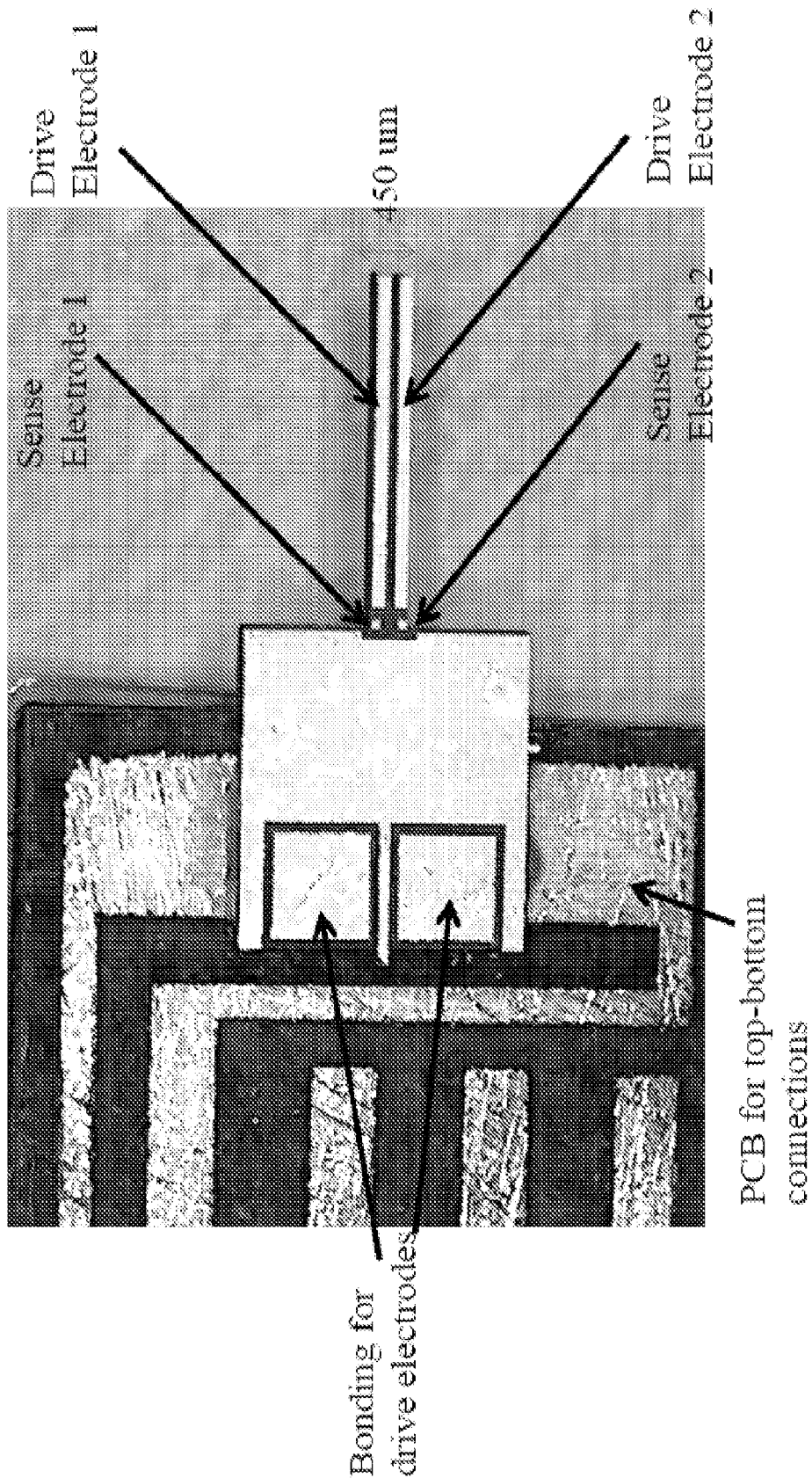
FIG. 25 shows an optical image of a PZT high voltage transformer comprised of a PZT structure including beams primarily acting as springs and masses.

FIG. 25 shows an optical image of a PZT high voltage transformer comprised of a PZT structure including beams primarily acting as springs and masses. In this device, the PZT beam is 450 um wide. As can be seen in FIG. 25, the two drive electrodes 1 and 2 are significantly longer than the two sense electrodes 1 and 2 where high voltages are obtained.

Figure 26:
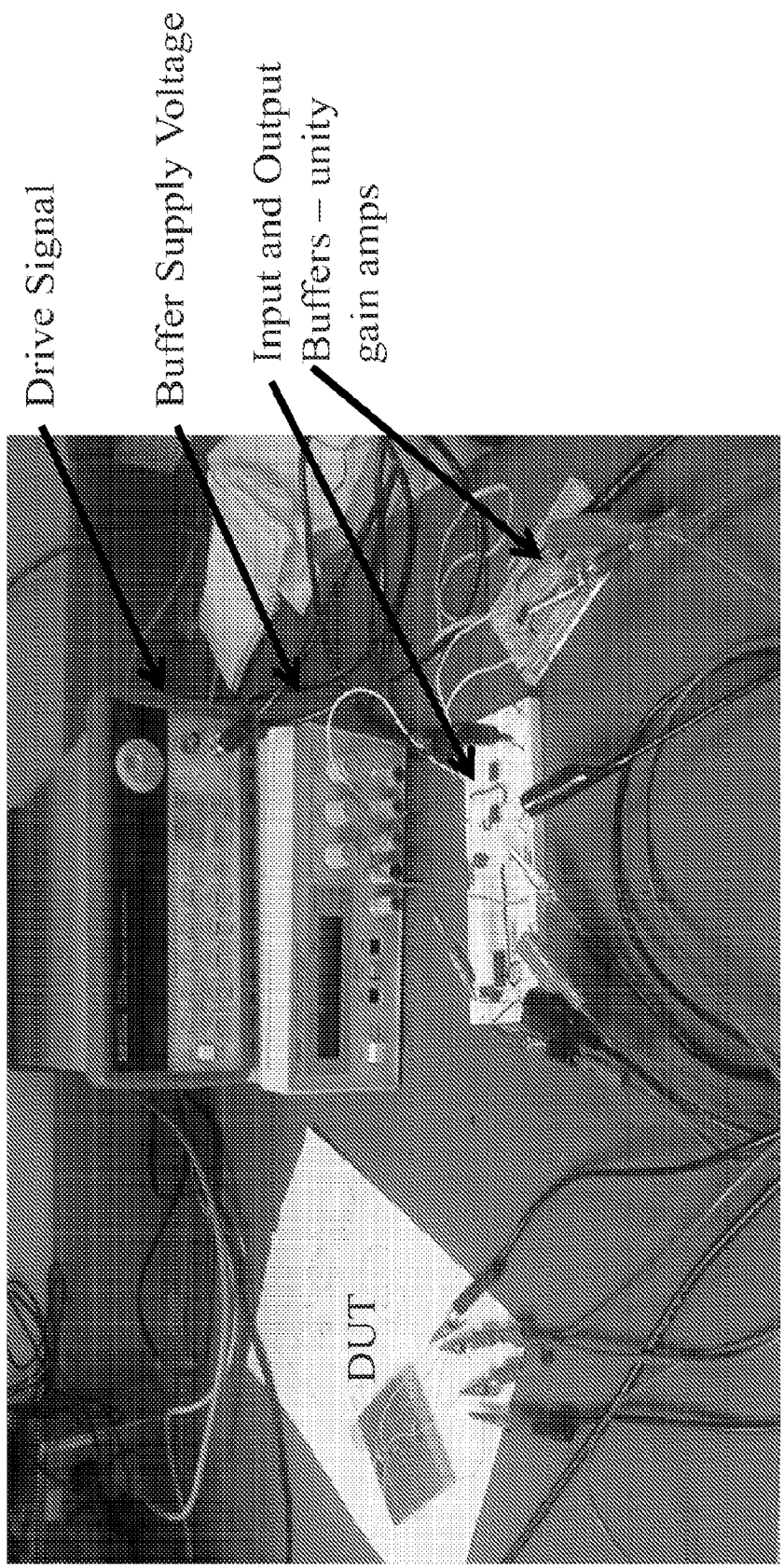
FIG. 26 shows an image of an exemplary test setup for a PZT transformer, such as the one shown in FIG. 25.

FIG. 26 shows an image of an exemplary test setup for a transformer, such as the one shown in FIG. 25. It is noticed that without input and output buffers for the device, the output was lowered due to loading. For example, 0.3V AC output is obtained for 1 V AC input drive. When the input and output buffers are used in the device, a gain in the output is obtained. For example, a gain of 1.4× was obtained for a device with electrodes patterned only on side of the PZT beam for applying signal and ground patterned on the other side of the PZT beam.

Figure 27:
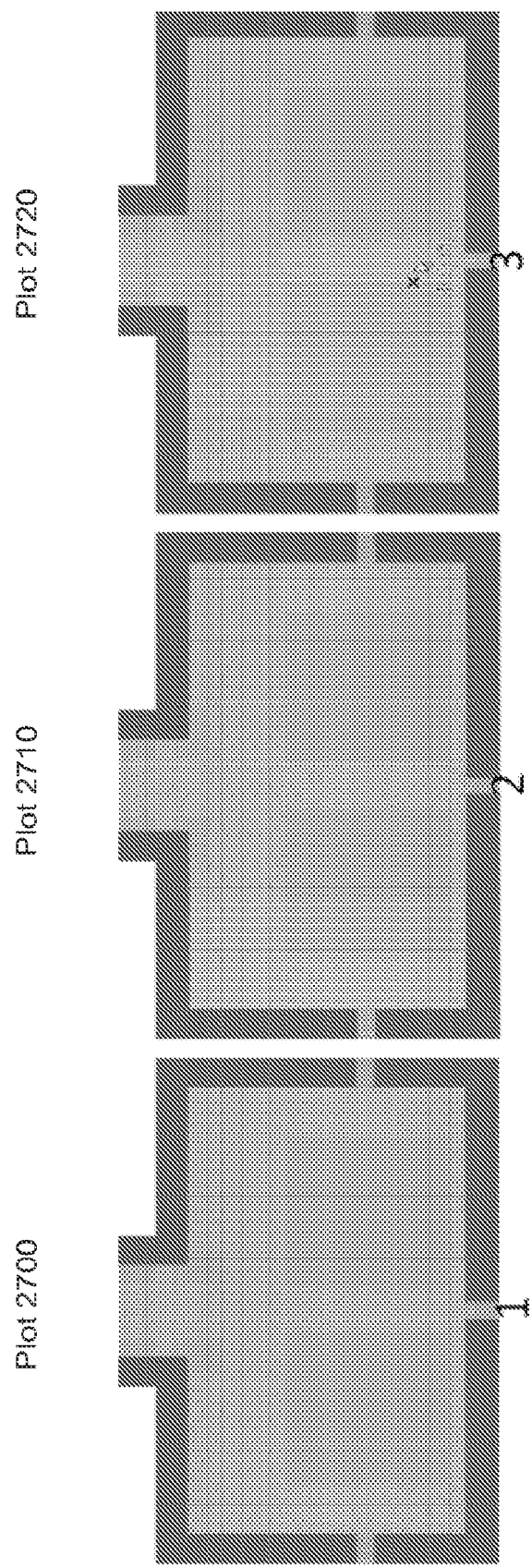
FIG. 27 shows different sense electrode configurations: a 150×150 square cut out from 450×300 rectangle (plot 1); a 150×300 cut in a 450×300 horizontal rectangle (plot 2); and a 150×300 cut in a 450×450 square (plot 3), all units in $um^2$.

FIG. 27 shows different sense electrode configurations: a 150×150 square cut out from 450×300 rectangle (plot 2700); a 150×300 cut in a 450×300 horizontal rectangle (plot 2710); and a 150×300 cut in a 450×450 square (plot 2720), all units in um$^2$. The different design configurations can be used to identify an optimal electrode size because stress generated at the anchor is not uniformly distributed near the anchor. Generally, larger electrodes can cause less charge to develop across the same area causing a lower voltage to be sensed.

Figure 28:
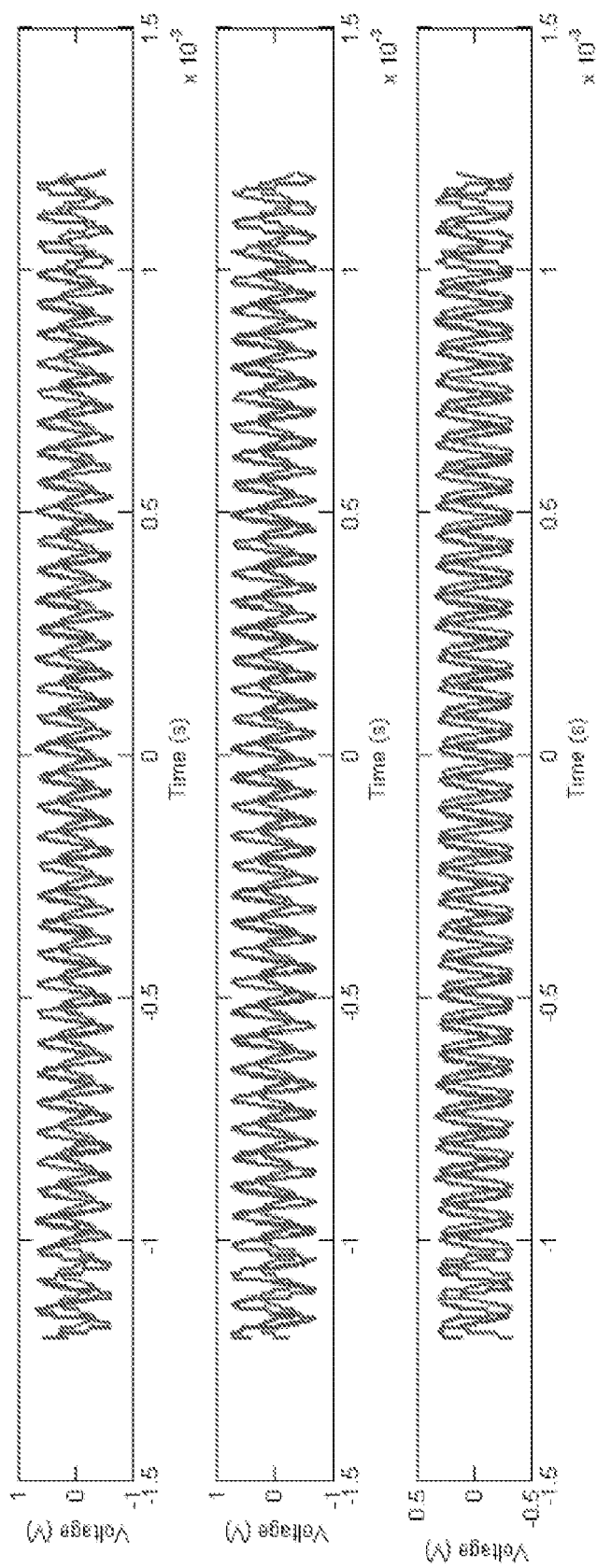
FIG. 28 shows exemplary simulation results of input voltages (red curves) and output voltages (blue curves) of the bimorph PT for the three configurations shown in FIG. 27.

FIG. 28 shows exemplary simulation results of input voltages (red curves) and output voltages (blue curves) of the bimorph PT for the three configurations shown in FIG. 27. As can be seen in FIG. 28, output gains are 0.95, 1.1 and 0.48, respectively for these three configurations. The 90 degree phase shift between input and output indicates that the output is the result of resonance, instead of feedthrough.

Figures 29A, 29B:
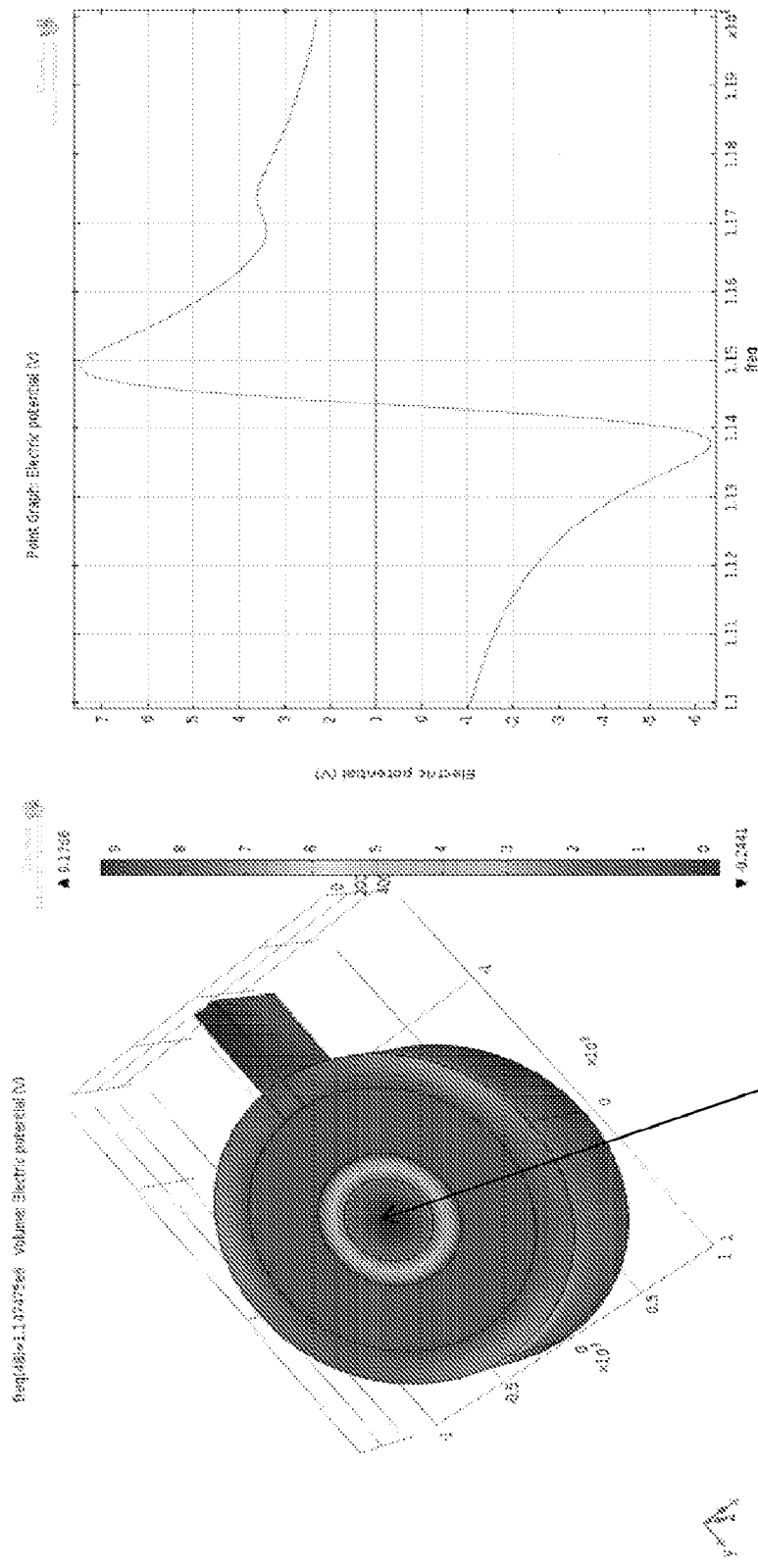
FIG. 29A shows an exemplary design of a high voltage disk transformer.
FIG. 29B shows exemplary simulation results of output voltage vs. frequency for the design of FIG. 29A.

FIG. 29A shows an exemplary design of a high voltage disk transformer. In this design, the input electrode is formed over the outer ring of the disk-shaped PZT while the output electrode is formed at the center of the disk-shaped PZT. As can be seen in FIG. 29A, the design allows for concentrating driving energy from the input electrode into the output electrode positioned at the center of the disk structure. FIG. 29B shows exemplary simulation results of output voltage vs frequency for the design of FIG. 29A.

Figure 30:
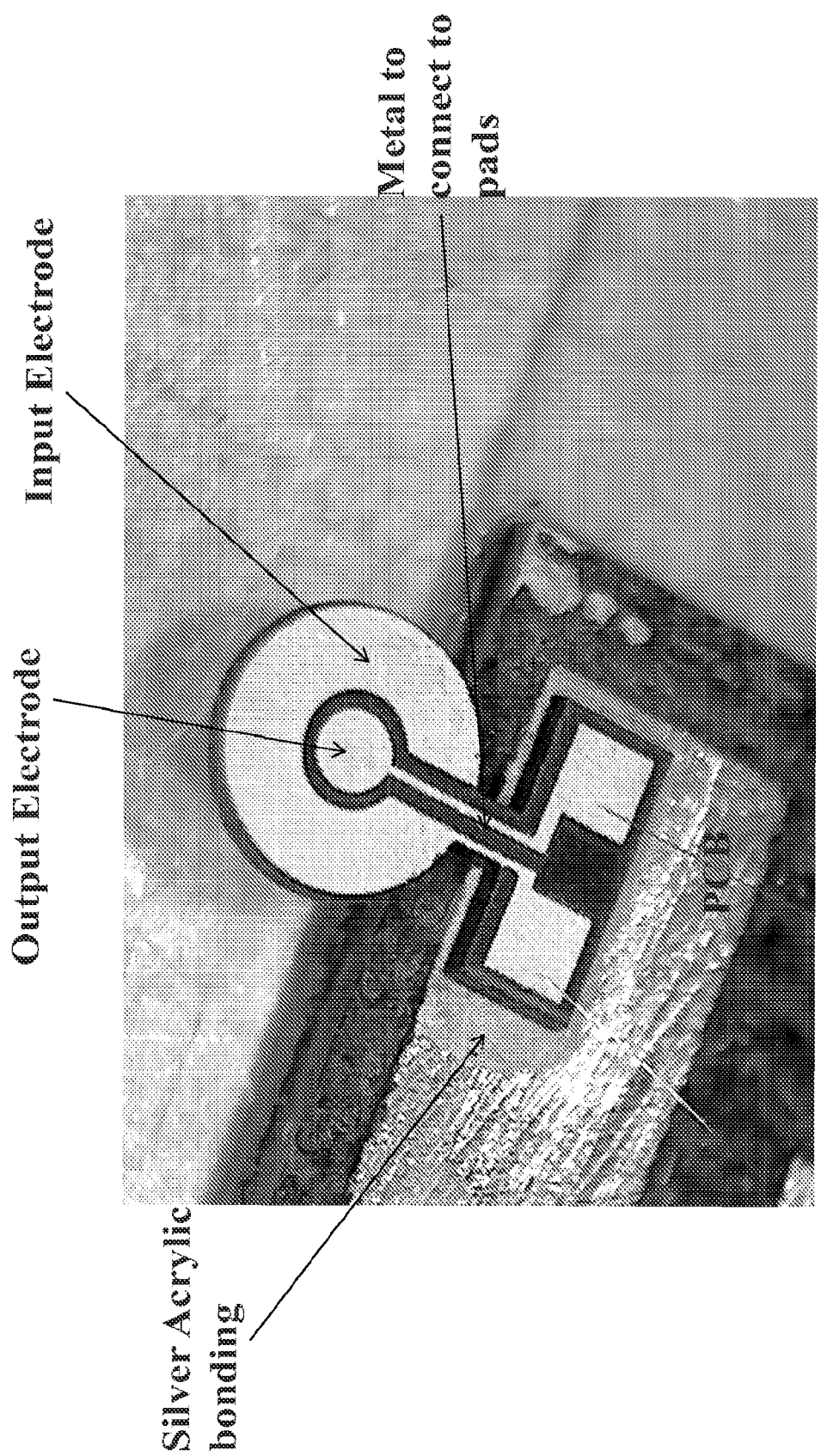
FIG. 30 shows an optical image of a fabricated high voltage disk transformer with the proposed input and output electrode configuration.
Figure 31:
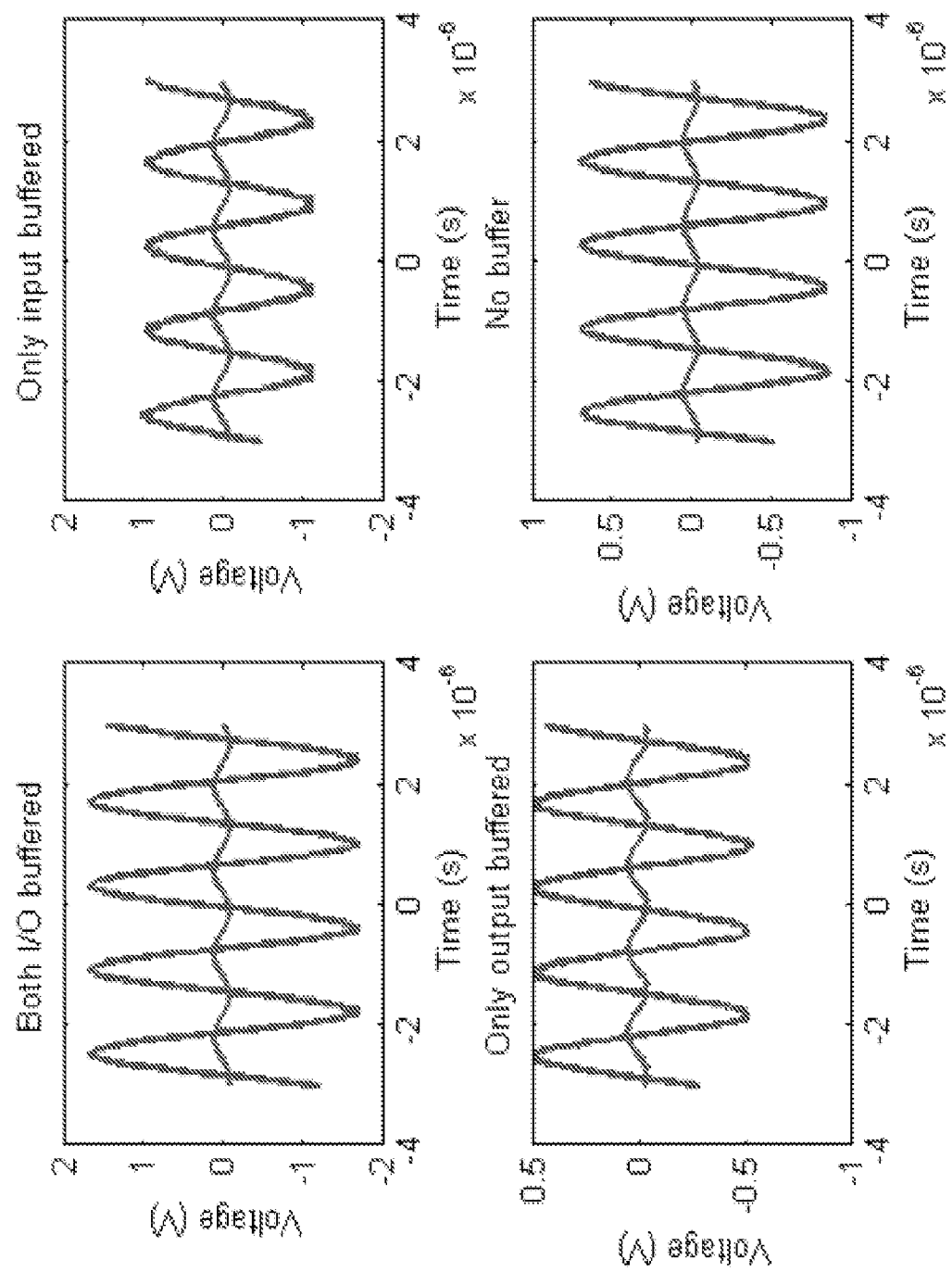
FIG. 31 shows exemplary measurement results of corresponding input and output voltage waveforms of the high voltage disk transformer in FIG. 30 with different input and output buffer inclusion options.

FIG. 30 shows an optical image of a fabricated high voltage disk transformer with the proposed input and output electrode configuration. FIG. 31 shows exemplary measurement results of corresponding input and output voltage waveforms of the high voltage disk transformer in FIG. 30 with different input and output buffer inclusion options. As can be observed from these I/O waveforms, using the disk resonator acting as a transformer, an output gain of ~16 at resonance can be obtained when both input and output buffers are used in the test setup.

When designing the proposed chip-based gas sensor, it is necessary to provide compact and low-power control and electronic interfaces for different modules within the chip-based gas sensor. For a proposed Ni-63 ionizer, no interface may be required because Ni-63 is a natural electron-emitting ionizer. For a proposed LiNbO$_3$ crystal ionizer or other pyroelectric ionizers, the control and interface circuits can be implemented using surface mount resistor attached to the LiNbO$_3$ crystal as heater, powered by a 5V battery. For a proposed PT ionizer, the control and interface circuits can be implemented using AD9833 chip-scale waveform generator to provide the AC drive signal, a 5 V battery, and crystal oscillator. For the proposed piezoelectric fan, the control and interface circuits can be substantially the same as those used for the PT ionizer.

Integration of Modules

Figure 32:
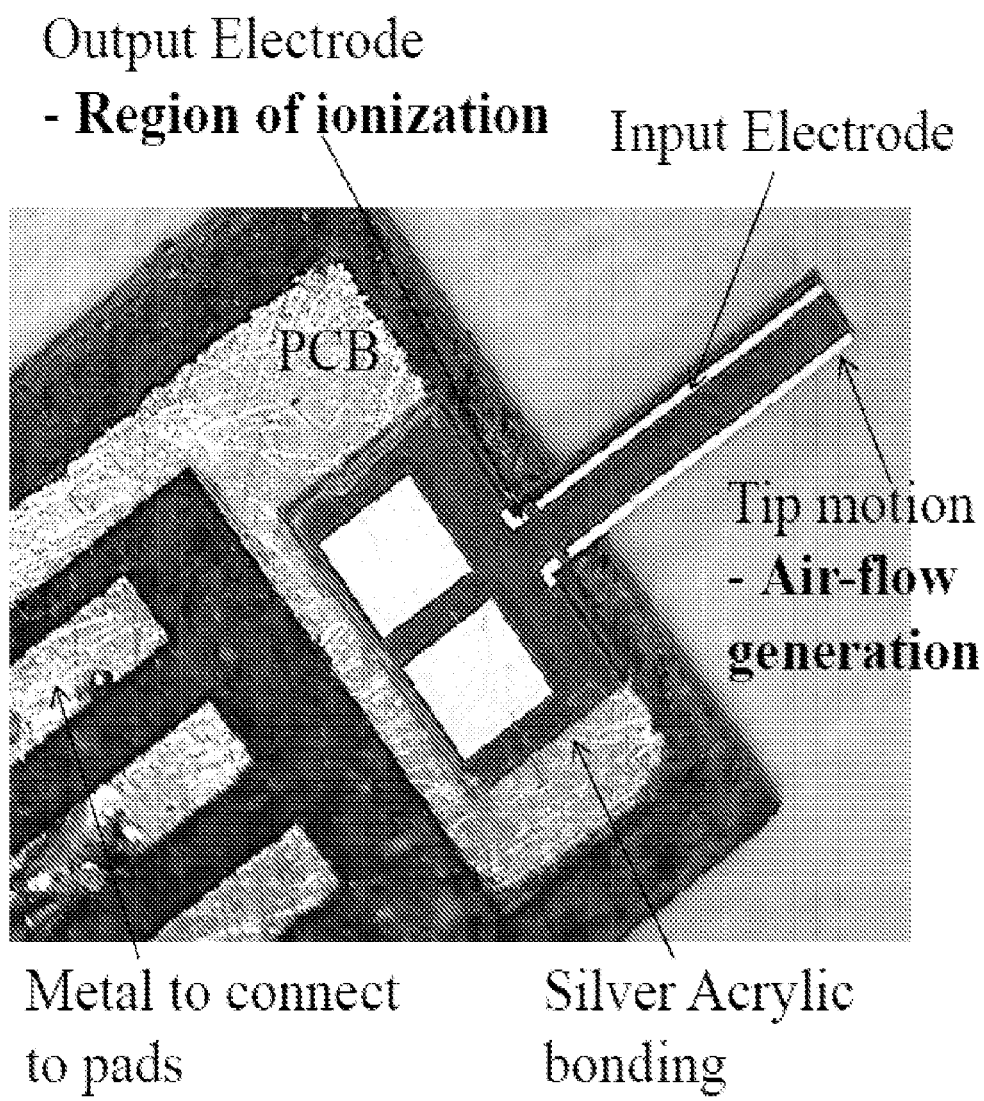
FIG. 32 shows an optical image of an integrated fan and ionizer based on the PZT high voltage generator.

FIG. 32 shows an optical image of an integrated fan and ionizer 3200 based on the same PZT high voltage generator described above. The proposed PZT high voltage generator as an ionizer includes a bimorph piezoelectric beam which can be driven by the same principle as the proposed piezoelectric micro-fan. As described previously, the region of ionization of this integrated fan and ionizer 3200 is located at the output electrodes. The cantilever shaped piezoelectric beam in this structure can be driven at the resonance of the beam by a drive signal applied to the input electrodes to cause motion at the tip of the beam, thereby generating an air-flow at the tip.

Because both the ionizer based on LiNBO$_3$ crystal and a pre-concentrator need heating to function and are successive stages in the proposed gas sensing system, to reduce power consumption, some implementations combine the LiNbO$_3$ crystal ionizer and the pre-concentrator. More specifically, the pre-concentrator material requires heat to desorb the gases that have been adsorbed in the material. This heat, typically generated using a resistor can drain the battery of a portable device. On the other hand, the LiNbO$_3$ crystal requires heat to build the electric field and requires battery energy. By combining the pre-concentrator with the LiNBO$_3$ crystal, one uses the same heat to desorb the gas and to generate the ionization field, thereby reducing the overall power usage per gas sensing cycle.

Figures 33A, 33B:
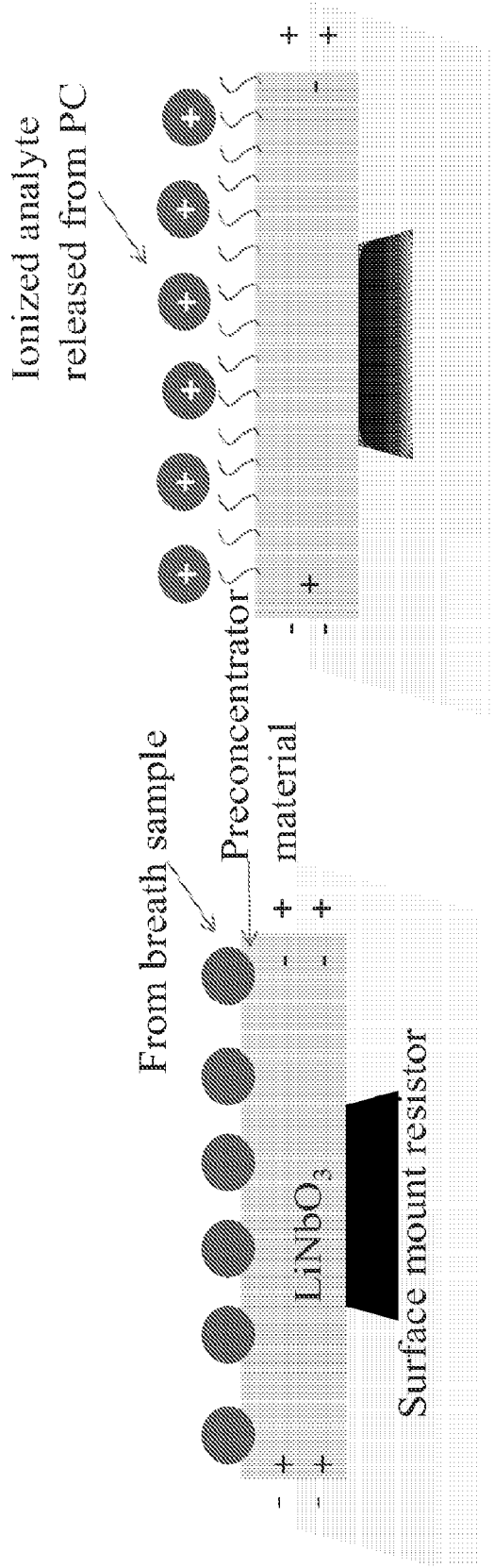
FIG. 33A shows an exemplary integrated ionizer and pre-concentrator for breath sample detection without tuning on surface mount resistive heater.
FIG. 33B shows the same integrated ionizer and pre-concentrator in FIG. 33A with the resistive heater turned on after completing sample collection over breath cycles.

FIG. 33A shows an exemplary integrated ionizer and pre-concentrator for breath sample detection without tuning on surface mount resistive heater. As can be seen in FIG. 33A, the integrated ionizer and pre-concentrator includes a LiNbO$_3$ crystal, a layer of pre-concentrator material coated on the top surface of the LiNbO$_3$ crystal, and a surface mount resistive heater attached to the bottom surface of the LiNbO$_3$ crystal. Over a sample collection period, analytes are accumulated on the pre-concentrator material which is attached on top of the LiNbO$_3$ crystal. Charges in the LiNbO$_3$ crystal due to poling are neutralized due to surface charges. Note that without heating, the breath analyses attached to the pre-concentrator material are not ionized. FIG. 33B shows the same integrated ionizer and pre-concentrator in FIG. 33A with the resistive heater turned on after completing sample collection over breath cycles. As can be seen in FIG. 33B, when the integrated ionizer and pre-concentrator is heated, the breath analyses are ionized and released from the pre-concentrator material, which can then flow into IMS ion-channel under the air-flow caused by the piezoelectric fan.

FIG. 34 presents a table including power consumptions for different modules within the chip-based gas sensor. As can be observed from the table, the proposed piezoelectric fan and various proposed ionizers all require very little power and can be operated with 5V or less voltages. Pre-concentrator consumes relatively large power which can be the bottom neck for low power requirement. One solution is to use the above-described integrated ionizer and pre-concentrator to replace the standalone pre-concentrator.

Graphene-Based Gas Sensing

Adsorption of volatile organic compounds (VOCs) on functionalized surfaces can be used to modulate or tune the physical and chemical properties of the functionalized surfaces. Graphene is a 2-D material with extraordinary electrical and mechanical properties. Graphene can adsorb molecules reversibly on its surface leading to electron-transfer between adsorbate and graphene, causing graphene conductance modulation. Furthermore, graphene can be patterned on micromachined suspended membranes to sense the mass of the adsorbed molecules which has been used for thin-film spun-on polymer thermogravimetry analysis.

FIG. 35A shows graphene patterned on micromachined suspended membranes.

More specifically, FIG. 35A shows pristine graphene-on-nitride. Graphene, when deposited on silicon nitride leaves vacant orbitals with electrons available for conduction. As can be seen in FIG. 35A, the out-of-plane p-orbitals contain electrons for conduction.

The described properties of graphene can be used to sense dynamic adsorption of various compounds on graphene. In the presence of these compounds, the graphene conductance reaches a steady-state which is different from the conductance prior to the adsorption. The molecules can eventually be desorbed by raising the temperature of graphene by the self Joule-heating of the graphene resistor, thus paving the way for a reusable gas sensing technique.

For example, FIG. 35B shows using graphene patterned micromachined suspended membranes as an electrical sensor to sense the mass of the adsorbed molecules without heating the structure. In the device shown in FIG. 35B, polymer-graphene interactions modulate electrical conduction. When the polymer is deposited on the graphene, the partial bonds and interactions between the polymer molecules and graphene affect the availability of conduction electrons, hence changing graphene resistance.

As another example, FIG. 35C shows using graphene patterned micromachined suspended membranes as an mechanical sensor to sense the mass of the adsorbed molecules while heating the structure with a resistive heater. In the device shown in FIG. 35C, polymer vaporization by resistive heating is sensed based on a resonance-frequency shift. More specifically, when the graphene resistance is used for heating the polymer, the resonance frequency of the membrane changes when the polymer evaporates, thereby enabling mass-sensing.

Figure 36:
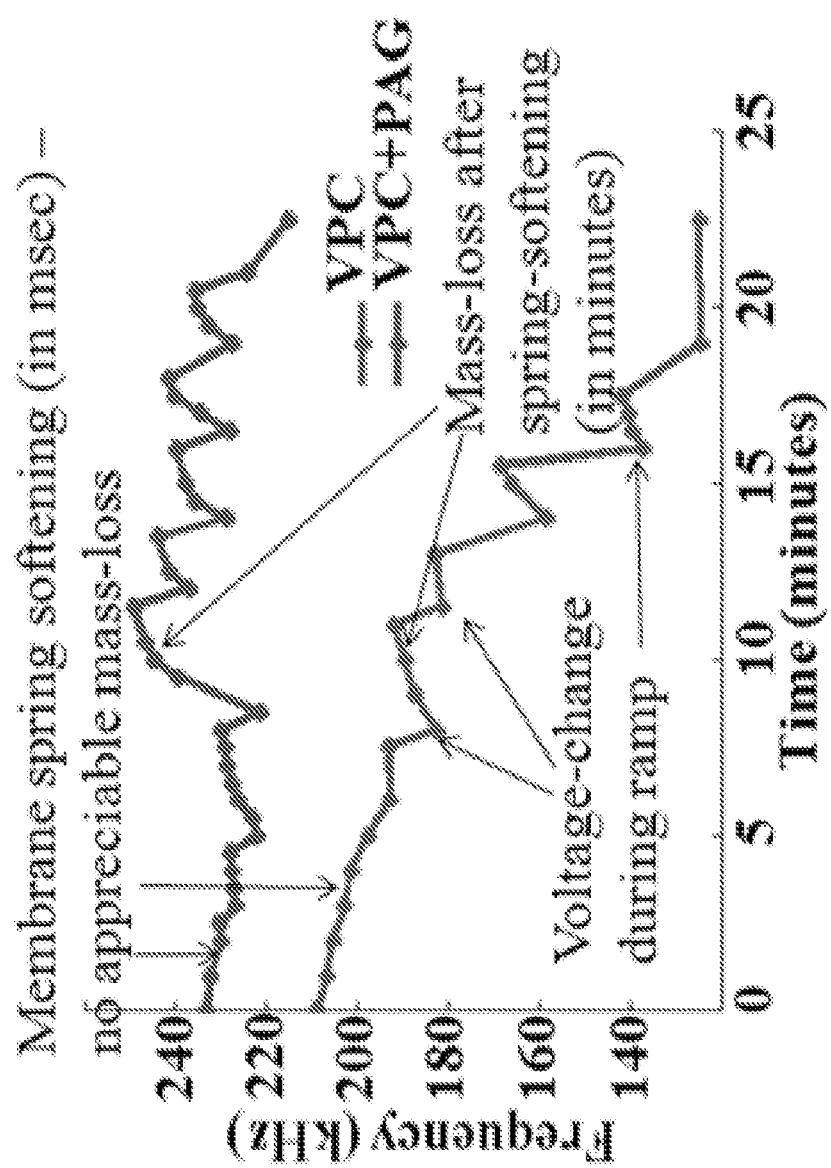
FIG. 36 shows exemplary results of mass sensing for different adsorbed materials on the graphene surface.

FIG. 36 shows exemplary results of mass sensing for different adsorbed materials on the graphene surface. As shown in FIG. 36, mass sensing measurement for the gas can be measured over-time and cycled thermally with input power to the graphene heater.

Figure 37:
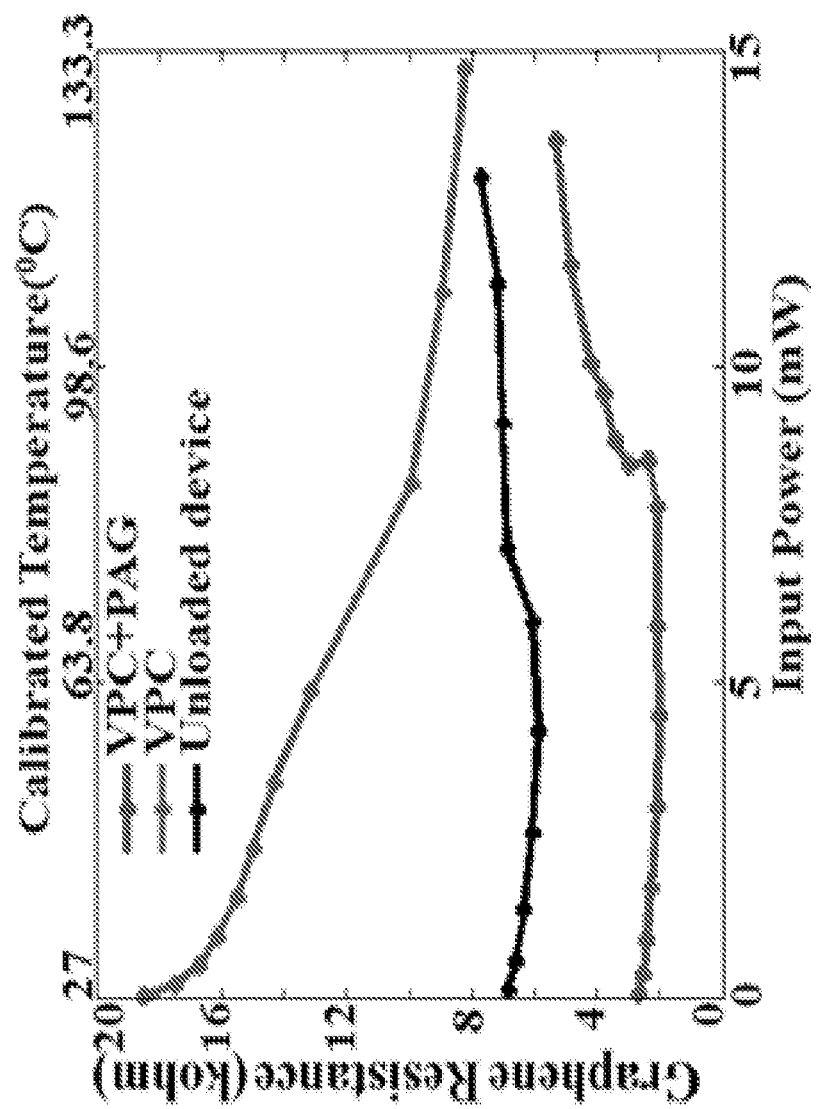
FIG. 37 shows exemplary results of electrical sensing for different adsorbed materials on the graphene surface.

FIG. 37 shows exemplary results of electrical sensing for different adsorbed materials on the graphene surface.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. An ion-gas sensor device, comprising:
a substrate including an array of pillars and troughs;
a microfan component including a first stack and a second stack of layers of a piezoelectric composite material formed on the pillars of the substrate and protruding over the troughs, the first stack of layers to sense the flow of ions in a gas and the second stack of layers actuate to drive the ions to a detection region of the device at a controlled flow rate;
a layer of a radioactive material formed in the trough of the substrate to ionize the gas when flowed above the layer; and
an array of electrode formed in the detection region to detect ion mobility of the ions of the gas.

2. The device as in claim 1, wherein the microfan component is configured to amplify the controlled flow rate based on resonance of the second stack of layers.

3. The device as in claim 1, comprising:
shedding air vortices located close to a tip of the second stack to control flow of the gas and re-circulate the gas in loops above or below a surface of the second stack.

4. The device as in claim 1, wherein the radioactive material includes a Ni-63 thin film.

5. The device as in claim 1, wherein the piezoelectric composite material includes a stack of SiO$_2$—TiPt-PZT-Pt layers.

6. The device as in claim 1, wherein:
the second stack of layers is configured to have a width of substantially 200 µm and a length of substantially 800 µm that protrudes over the trough of the substrate, and the first stack of layers is configured to have a width of substantially 200 µm and a length of substantially 1000 µm that protrudes over the trough of the substrate.

7. A chip scale gas sensor, comprising:
a pre-concentration module to collect and concentrate a gas-phase chemical for analysis;
a piezoelectric fan to produce an air-flow through acoustic streaming to drive the gas-phase chemical released by the pre-concentration module to one or more downstream modules;
an ionizer downstream from the piezoelectric fan to ionize the gas-phase chemical; and
a gas sensor downstream from the piezoelectric fan and the ionizer to detect the ionized gas-phase chemical driven by the piezoelectric fan.

8. The chip scale gas sensor of claim 7, wherein the piezoelectric fan includes a stack of thin-film layers that includes a thin-film piezoelectric layer.

9. The chip scale gas sensor of claim 8, wherein the stack of thin-film layers is shaped as a cantilever, wherein the cantilever is anchored at a first end of the cantilever and actuated to move up and down at a second end of the cantilever.

10. The chip scale gas sensor of claim 8, wherein the ionizer is positioned directly under the second end of the cantilever.

11. The chip scale gas sensor of claim 7, wherein the piezoelectric fan includes a thin-film piezoelectric-$SiO_2$ composite unimorph.

12. The chip scale gas sensor of claim 7, wherein the piezoelectric fan comprises a first stack of thin-film layers including a first piezoelectric-$SiO_2$ composite unimorph and a second stack of thin-film layers positioned in the vicinity of the first stack of thin-film layers and including a second piezoelectric-$SiO_2$ composite unimorph, wherein the first stack of thin-film layers is configured to actuate to drive the ionized gas-phase chemical to the gas sensor, and wherein the second stack of thin-film layers is configured to measure an air-flow near the first stack of thin-film layers to provide feedback signal for controlling a drive signal that actuates the first stack of thin-film layers.

13. The chip scale gas sensor of claim 12, wherein the first stack of thin-film layers is shaped as a first cantilever, and the second stack of thin-film layers is shaped as a second cantilever, wherein the first and second cantilevers are substantially parallel to each other.

14. The chip scale gas sensor of claim 12, wherein the ionizer is positioned directly under a free end of the first cantilever.

15. The chip scale gas sensor of claim 7, wherein the ionizer includes a layer of radioactive material.

16. The chip scale gas sensor of claim 7, wherein the ionizer includes a radioactive Ni-63 thin-film layer.

17. The chip scale gas sensor of claim 16, wherein the ionizer further includes a non-radioactive nickel layer, and wherein the radioactive Ni-63 thin-film layer is adhered to the non-radioactive nickel layer.

18. The chip scale gas sensor of claim 17, wherein the ionizer further includes a second non-radioactive nickel layer electroplated over the radioactive Ni-63 thin-film layer.

19. The chip scale gas sensor of claim 7, wherein the ionizer includes a pyroelectric material which enables ionization of a compound when the pyroelectric material is undergoing a pyroelectric process.

20. The chip scale gas sensor of claim 19, wherein the pyroelectric material includes a lithium niobate ($LiNbO_3$) crystal.

21. The chip scale gas sensor of claim 20, wherein the $LiNbO_3$ crystal is cut to expose +z plate of the $LiNbO_3$ crystal.

22. The chip scale gas sensor of claim 19, wherein the ionizer further includes a resistive heater attached to the pyroelectric material to heat the pyroelectric material in a pyroelectric process.

23. The chip scale gas sensor of claim 7, wherein the ionizer includes a piezo-transformer formed by a piezoelectric structure poled along two different axes of the piezoelectric structure.

24. The chip scale gas sensor of claim 23, wherein the piezo-transformer further includes one or more drive electrodes positioned over a first region of the piezoelectric structure and one or more sense electrodes positioned over a second region of the piezoelectric structure, wherein the piezo-transformer is configured to concentrate driving energy from the drive electrodes into the sense electrode to obtain an output voltage gain.

25. The chip scale gas sensor of claim 23, wherein the piezoelectric structure is a bulk piezoelectric beam.

26. The chip scale gas sensor of claim 22, wherein the piezoelectric structure is a bulk piezoelectric disk.

27. The chip scale gas sensor of claim 7, wherein piezoelectric fan is made of a bulk piezoelectric material.

28. The chip scale gas sensor of claim 7, wherein the gas sensor is an ion-mobility spectrometry (IMS).

29. A chip scale gas sensor, comprising:
an integrated pre-concentration and ionization module that includes:
a first material layer to collect and concentrate a gas-phase molecules for analysis; and
a second material layer underneath the first material layer to ionize the gas-phase molecules;
a piezoelectric fan to produce an air-flow through acoustic streaming to drive ionized gas-phase molecules released by the integrated pre-concentration and ionization module to one or more downstream modules; and
a gas sensor downstream from the piezoelectric fan to detect the ionized gas-phase molecules driven by the piezoelectric fan.

30. The chip scale gas sensor of claim 29, wherein the second material layer is a $LiNbO_3$ crystal.

31. The chip scale gas sensor of claim 29, wherein the first material layer is a functionalized material for molecule collection and concentration.

32. The chip scale gas sensor of claim 31, wherein the integrated pre-concentration and ionization module further includes a resistive heater placed underneath the second material layer.

33. The chip scale gas sensor of claim 32, wherein the integrated pre-concentration and ionization module is configured such that the heat generated by the resistive heater both triggers ionization of the gas-phase molecules adsorbed in the functionalized material by the ionization module and the ionized gas-phase molecules adsorbed in the functionalized material to be released from the functionalized material.

34. A chip scale gas sensor, comprising:
a pre-concentration module to collect and concentrate a gas-phase chemical for analysis;
an integrated air pump and ionization module that includes a piezoelectric fan to produce an air-flow through acoustic streaming to drive the gas-phase chemical released by the pre-concentration module to one or more downstream modules, wherein the piezoelectric fan includes a region configured to ionize the gas-phase chemical driven by the piezoelectric fan; and a gas sensor downstream from the integrated air pump and ionization module to detect the ionized gas-phase chemical driven by the piezoelectric fan.

35. The chip scale gas sensor of claim 34, wherein the integrated air pump and ionization module includes a PZT high voltage transformer.

* * * * *

UNITED STATES PATENT AND TRADEMARK OFFICE
CERTIFICATE OF CORRECTION

PATENT NO. : 9,683,967 B2
APPLICATION NO. : 15/114814
DATED : June 20, 2017
INVENTOR(S) : Amit Lal and Ved Gund Page 1 of 1

It is certified that error appears in the above-identified patent and that said Letters Patent is hereby corrected as shown below:

In Column 1, after Line 11, please insert the following:

-- GOVERNMENT SUPPORT STATEMENT
This invention was made with government support under W32P4Q-12-1-0003 awarded by the U.S. Army. The government has certain rights in the invention. --

Signed and Sealed this
Twenty-second Day of May, 2018

Andrei Iancu
*Director of the United States Patent and Trademark Office*